(12) United States Patent
Pudil et al.

(10) Patent No.: US 11,944,733 B2
(45) Date of Patent: Apr. 2, 2024

(54) SODIUM AND BICARBONATE CONTROL

(71) Applicants: Bellco SRL, Mirandola (IT); Medtronic, Inc., Minneapolis, MN (US)

(72) Inventors: Bryant J Pudil, Plymouth, MN (US); Mariangela Iatalese, Fortore (IT)

(73) Assignee: Mozarc Medical US LLC, Minneapolis, MN (US)

( * ) Notice: Subject to any disclaimer, the term of this patent is extended or adjusted under 35 U.S.C. 154(b) by 0 days.

(21) Appl. No.: 17/529,809

(22) Filed: Nov. 18, 2021

(65) Prior Publication Data
US 2023/0149607 A1    May 18, 2023

(51) Int. Cl.
*A61M 1/16* (2006.01)

(52) U.S. Cl.
CPC ........ *A61M 1/1696* (2013.01); *A61M 1/1607* (2014.02); *A61M 1/1658* (2013.01); *A61M 2205/3324* (2013.01)

(58) Field of Classification Search
CPC .............. A61M 1/1607; A61M 1/1658; A61M 1/1696; A61M 2205/3324; A61M 2205/50; A61M 2230/208; A61M 1/1609; A61M 2205/3317; A61M 1/1656; A61M 1/287; A61M 1/1666; A61M 1/169; A61M 1/1566; A61M 1/36224
See application file for complete search history.

(56) References Cited

U.S. PATENT DOCUMENTS

| | | |
|---|---|---|
| 3,602,222 A | 8/1971 | Herndon |
| 3,608,729 A | 9/1971 | Haselden |
| 3,669,878 A | 6/1972 | Marantz |
| 3,669,880 A | 6/1972 | Marantz |
| 3,730,183 A | 5/1973 | Goldsmith |
| 3,754,867 A | 8/1973 | Guenther |
| 3,850,835 A | 11/1974 | Marantz |
| 3,884,808 A | 5/1975 | Scott |
| 3,989,622 A | 11/1976 | Marantz |
| 4,060,485 A | 11/1977 | Eaton |
| 4,371,385 A | 2/1983 | Johnson |
| 4,374,382 A | 2/1983 | Markowitz |
| 4,381,999 A | 5/1983 | Boucher |
| 4,460,555 A | 7/1984 | Thompson |
| 4,556,063 A | 12/1985 | Thompson |

(Continued)

FOREIGN PATENT DOCUMENTS

| | | |
|---|---|---|
| CN | 101193667 | 6/2008 |
| DE | 3224823 | 1/1984 |

(Continued)

OTHER PUBLICATIONS

[NPL105] Brynda, et. al., The detection of toman 2-microglebuiin by grating coupler immunosensor with three dimensional antibody networks. Biosensors & Bioelectronics, 1999, 363-368, 14(4).

(Continued)

*Primary Examiner* — Pranav N Patel

(57) ABSTRACT

The disclosure relates to systems and methods for controlling the sodium and bicarbonate concentrations in a dialysate. The systems and methods can use conductivity sensors to control the addition of water and bicarbonate to accurately control the final concentrations of both sodium and bicarbonate.

18 Claims, 8 Drawing Sheets

(56) References Cited

U.S. PATENT DOCUMENTS

| | | |
|---|---|---|
| 4,562,751 A | 1/1986 | Nason |
| 4,581,141 A | 4/1986 | Ash |
| 4,650,587 A | 3/1987 | Polak |
| 4,661,246 A | 4/1987 | Ash |
| 4,678,408 A | 7/1987 | Mason |
| 4,685,903 A | 8/1987 | Cable |
| 4,747,822 A | 5/1988 | Peabody |
| 4,750,494 A | 6/1988 | King |
| 4,772,560 A | 9/1988 | Attar |
| 4,799,493 A | 1/1989 | DuFault |
| 4,826,663 A | 5/1989 | Alberti |
| 4,828,693 A | 5/1989 | Lindsay |
| 5,032,265 A | 7/1991 | Jha |
| 5,080,653 A | 1/1992 | Voss |
| 5,091,642 A | 2/1992 | Chow |
| 5,092,886 A | 3/1992 | Dobos-Hardy |
| 5,097,122 A | 3/1992 | Coiman |
| 5,127,404 A | 7/1992 | Wyborny |
| 5,141,493 A | 8/1992 | Jacobsen |
| 5,284,470 A | 2/1994 | Beltz |
| 5,302,288 A | 4/1994 | Meidl |
| 5,305,745 A | 4/1994 | Zacouto |
| 5,318,750 A | 6/1994 | Lascombes |
| 5,468,388 A | 11/1995 | Goddard |
| 5,507,723 A | 4/1996 | Keshaviah |
| 5,643,201 A | 7/1997 | Peabody |
| 5,651,893 A | 7/1997 | Kenley |
| 5,683,432 A | 11/1997 | Goedeke |
| 5,744,031 A | 4/1998 | Bene |
| 5,762,782 A | 6/1998 | Kenley |
| 5,819,007 A | 10/1998 | Elghazzawi |
| 5,902,336 A | 5/1999 | Mishkin |
| 5,944,684 A | 8/1999 | Roberts |
| 5,987,352 A | 11/1999 | Klein |
| 6,048,732 A | 4/2000 | Anslyn |
| 6,052,622 A | 4/2000 | Holmstrom |
| 6,058,331 A | 5/2000 | King |
| 6,156,002 A | 12/2000 | Polaschegg |
| 6,230,059 B1 | 5/2001 | Duffin |
| 6,248,093 B1 | 6/2001 | Moberg |
| 6,254,567 B1 | 7/2001 | Treu |
| 6,321,101 B1 | 11/2001 | Holmstrom |
| 6,362,591 B1 | 3/2002 | Moberg |
| 6,363,279 B1 | 3/2002 | Ben-Haim |
| 6,505,075 B1 | 1/2003 | Weiner |
| 6,554,798 B1 | 4/2003 | Mann |
| 6,555,986 B2 | 4/2003 | Moberg |
| 6,589,229 B1 | 7/2003 | Connelly |
| 6,602,399 B1 | 8/2003 | Fromherz |
| 6,609,023 B1 | 8/2003 | Fischell |
| 6,627,164 B1 | 9/2003 | Wong |
| 6,645,191 B1 | 11/2003 | Knerr |
| 6,676,608 B1 | 1/2004 | Keren |
| 6,689,083 B1 | 2/2004 | Gelfand |
| 6,706,007 B2 | 3/2004 | Gelfand |
| 6,711,439 B1 | 3/2004 | Bradley |
| 6,726,647 B1 | 4/2004 | Sternby |
| 6,780,322 B1 | 8/2004 | Bissler |
| 6,818,196 B2 | 11/2004 | Wong |
| 6,878,283 B2 | 4/2005 | Thompson |
| 6,887,214 B1 | 5/2005 | Levin |
| 6,890,315 B1 | 5/2005 | Levin |
| 6,960,179 B2 | 11/2005 | Gura |
| 7,074,332 B2 | 7/2006 | Summerton |
| 7,077,819 B1 | 7/2006 | Goldau |
| 7,131,956 B1 | 11/2006 | Pirazzoli |
| 7,175,809 B2 | 2/2007 | Gelfand |
| 7,208,092 B2 | 4/2007 | Micheli |
| 7,276,042 B2 | 10/2007 | Polaschegg |
| 7,399,289 B2 | 7/2008 | Gelfand |
| 7,404,799 B1 | 7/2008 | Koh |
| 7,500,958 B2 | 3/2009 | Asbrink |
| 7,566,432 B2 | 7/2009 | Wong |
| 7,575,564 B2 | 8/2009 | Childers |
| 7,610,086 B1 | 10/2009 | Ke |
| 7,674,231 B2 | 3/2010 | Mccombie |
| 7,704,361 B2 | 4/2010 | Garde |
| 7,736,507 B2 | 6/2010 | Wong |
| 7,744,553 B2 | 6/2010 | Kelly |
| 7,754,852 B2 | 7/2010 | Burnett |
| 7,756,572 B1 | 7/2010 | Fard |
| 7,775,983 B2 | 8/2010 | Zhang |
| 7,775,986 B2 | 8/2010 | Roeher |
| 7,776,210 B2 | 8/2010 | Rosenbaum |
| 7,785,463 B2 | 8/2010 | Bissler |
| 7,794,141 B2 | 9/2010 | Perry |
| 7,850,635 B2 | 12/2010 | Polaschegg |
| 7,857,976 B2 | 12/2010 | Bissler |
| 7,867,214 B2 | 1/2011 | Childers |
| 7,896,831 B2 | 3/2011 | Sternby |
| 7,922,686 B2 | 4/2011 | Childers |
| 7,922,911 B2 | 4/2011 | Micheli |
| 7,947,179 B2 | 5/2011 | Rosenbaum |
| 7,955,291 B2 | 6/2011 | Sternby |
| 7,967,022 B2 | 6/2011 | Grant |
| 7,981,082 B2 | 7/2011 | Wang |
| 8,034,161 B2 | 10/2011 | Gura |
| 8,070,709 B2 | 12/2011 | Childers |
| 8,096,969 B2 | 1/2012 | Roberts |
| 8,105,260 B2 | 1/2012 | Tonelli |
| 8,183,046 B2 | 5/2012 | Lu |
| 8,187,250 B2 | 5/2012 | Roberts |
| 8,197,439 B2 | 6/2012 | Wang |
| 8,202,241 B2 | 6/2012 | Karakama |
| 8,246,826 B2 | 8/2012 | Wilt |
| 8,273,049 B2 | 9/2012 | Demers |
| 8,282,828 B2 | 10/2012 | Wallenas |
| 8,292,594 B2 | 10/2012 | Tracey |
| 8,313,642 B2 | 11/2012 | Yu |
| 8,317,492 B2 | 11/2012 | Demers |
| 8,357,113 B2 | 1/2013 | Childers |
| 8,366,316 B2 | 2/2013 | Kamen |
| 8,366,655 B2 | 2/2013 | Kamen |
| 8,404,091 B2 | 3/2013 | Ding |
| 8,409,441 B2 | 4/2013 | Wilt |
| 8,496,809 B2 | 7/2013 | Roger |
| 8,499,780 B2 | 8/2013 | Wilt |
| 8,500,676 B2 | 8/2013 | Jansson |
| 8,512,271 B2 | 8/2013 | Moissl |
| 8,518,260 B2 | 8/2013 | Raimann |
| 8,521,482 B2 | 8/2013 | Akonur |
| 8,535,525 B2 | 9/2013 | Heyes |
| 8,560,510 B2 | 10/2013 | Brueggerhoff |
| 8,580,112 B2 | 11/2013 | Updyke |
| 8,597,227 B2 | 12/2013 | Childers |
| 8,696,626 B2 | 4/2014 | Kirsch |
| 8,903,492 B2 | 12/2014 | Soykan |
| 8,926,542 B2 | 1/2015 | Gerber |
| 2002/0016550 A1 | 2/2002 | Sweeney |
| 2002/0042561 A1 | 4/2002 | Schulman |
| 2002/0112609 A1 | 8/2002 | Wong |
| 2003/0028089 A1 | 4/2003 | Galley |
| 2003/0069481 A1 | 4/2003 | Hervy |
| 2003/0080059 A1 | 5/2003 | Peterson |
| 2003/0097086 A1 | 5/2003 | Gura |
| 2003/0105435 A1 | 6/2003 | Taylor |
| 2003/0113931 A1 | 6/2003 | Pan |
| 2003/0114787 A1 | 6/2003 | Gura |
| 2003/0187479 A1 | 10/2003 | Thong |
| 2004/0019312 A1 | 1/2004 | Childers |
| 2004/0060865 A1 | 4/2004 | Callan |
| 2004/0068219 A1 | 4/2004 | Summerton |
| 2004/0099593 A1 | 5/2004 | DePaolis |
| 2004/0147900 A1 | 7/2004 | Polaschegg |
| 2004/0168969 A1 | 9/2004 | Sternby |
| 2004/0215090 A1 | 10/2004 | Erkkila |
| 2005/0065760 A1 | 3/2005 | Murtfeldt |
| 2005/0113796 A1 | 5/2005 | Taylor |
| 2005/0126961 A1 | 6/2005 | Bissler |
| 2005/0131331 A1 | 6/2005 | Kelly |
| 2005/0126998 A1 | 7/2005 | Childers |
| 2005/0150832 A1 | 7/2005 | Tsukamoto |
| 2005/0214863 A1 | 9/2005 | McDevitt |
| 2005/0234354 A1 | 10/2005 | Rowlandson |

(56) References Cited

U.S. PATENT DOCUMENTS

| | | |
|---|---|---|
| 2005/0234357 A1 | 10/2005 | Xue |
| 2005/0234381 A1 | 10/2005 | Niemetz |
| 2005/0234534 A1 | 10/2005 | Rowlandson |
| 2005/0236330 A1 | 10/2005 | Nier |
| 2005/0265895 A1 | 12/2005 | Kopelman |
| 2005/0274658 A1 | 12/2005 | Rosenbaum |
| 2006/0025661 A1 | 2/2006 | Sweeney |
| 2006/0025748 A1 | 2/2006 | Ye |
| 2006/0217771 A1 | 2/2006 | Soykan |
| 2006/0058731 A1 | 3/2006 | Burnett |
| 2006/0191850 A1 | 8/2006 | Bosetto |
| 2006/0195064 A1 | 8/2006 | Plahey |
| 2006/0226079 A1 | 10/2006 | Mori |
| 2006/0241709 A1 | 10/2006 | Soykan |
| 2006/0247548 A1 | 11/2006 | Sarkar |
| 2006/0264894 A1 | 11/2006 | Moberg |
| 2007/0007208 A1 | 1/2007 | Brugger |
| 2007/0038138 A1 | 2/2007 | Gill |
| 2007/0066928 A1 | 3/2007 | Lannoy |
| 2007/0073168 A1 | 3/2007 | Zhang |
| 2007/0138011 A1 | 6/2007 | Hofmann |
| 2007/0161113 A1 | 7/2007 | Ash |
| 2007/0175827 A1 | 8/2007 | Wariar |
| 2007/0179431 A1 | 8/2007 | Roberts |
| 2007/0213653 A1 | 9/2007 | Childers |
| 2007/0213665 A1* | 9/2007 | Curtin ............... A61M 1/28 604/174 |
| 2007/0215545 A1 | 9/2007 | Bissler |
| 2007/0255250 A1 | 11/2007 | Moberg |
| 2007/0276270 A1 | 11/2007 | Tran |
| 2008/0006570 A1 | 1/2008 | Gura |
| 2008/0021337 A1 | 1/2008 | Li |
| 2008/0053905 A9 | 3/2008 | Brugger |
| 2008/0067132 A1 | 3/2008 | Ross |
| 2008/0093276 A1 | 4/2008 | Roger |
| 2008/0200866 A1 | 8/2008 | Prisco |
| 2008/0215247 A1 | 9/2008 | Tonelli |
| 2008/0253427 A1 | 10/2008 | Kamen |
| 2009/0020471 A1 | 1/2009 | Tsukamoto |
| 2009/0036825 A1 | 2/2009 | Petersen |
| 2009/0101577 A1 | 4/2009 | Fulkerson |
| 2009/0124869 A1 | 5/2009 | Hu |
| 2009/0124963 A1 | 5/2009 | Hogard |
| 2009/0127193 A1 | 5/2009 | Updyke |
| 2009/0171261 A1 | 7/2009 | Sternby |
| 2009/0264776 A1 | 10/2009 | Vardy |
| 2009/0275849 A1 | 11/2009 | Stewart |
| 2009/0275883 A1 | 11/2009 | Chapman |
| 2009/0281484 A1 | 11/2009 | Childers |
| 2009/0282980 A1 | 11/2009 | Gura |
| 2009/0314063 A1 | 12/2009 | Sternby |
| 2010/0004588 A1 | 1/2010 | Yeh |
| 2010/0010429 A1 | 1/2010 | Childers |
| 2010/0042035 A1 | 2/2010 | Moissl |
| 2010/0076398 A1 | 3/2010 | Scheurer |
| 2010/0078381 A1 | 4/2010 | Merchant |
| 2010/0078387 A1 | 4/2010 | Wong |
| 2010/0084330 A1 | 4/2010 | Wong |
| 2010/0087771 A1 | 4/2010 | Karakama |
| 2010/0094158 A1 | 4/2010 | Solem |
| 2010/0113891 A1 | 5/2010 | Barrett |
| 2010/0114012 A1 | 5/2010 | Sandford |
| 2010/0137693 A1 | 6/2010 | Porras |
| 2010/0137782 A1 | 6/2010 | Jansson |
| 2010/0168546 A1 | 7/2010 | Kamath |
| 2010/0217180 A1 | 8/2010 | Akonur |
| 2010/0217181 A1 | 8/2010 | Roberts |
| 2010/0224492 A1 | 9/2010 | Ding |
| 2010/0234795 A1 | 9/2010 | Wallenas |
| 2010/0241045 A1 | 9/2010 | Kelly |
| 2010/0264086 A1 | 10/2010 | Noack |
| 2010/0312172 A1 | 12/2010 | Hoffman |
| 2011/0017665 A1 | 1/2011 | Updyke |
| 2011/0048949 A1 | 3/2011 | Ding et al. |
| 2011/0066006 A1 | 3/2011 | Banet |
| 2011/0066043 A1 | 3/2011 | Banet |
| 2011/0071465 A1 | 3/2011 | Wang |
| 2011/0077574 A1 | 3/2011 | Sigg |
| 2011/0077575 A1 | 3/2011 | Kraemer |
| 2011/0079558 A1 | 4/2011 | Raimann |
| 2011/0081728 A1 | 4/2011 | Putnam |
| 2011/0087187 A1 | 4/2011 | Beck |
| 2011/0100909 A1 | 5/2011 | Stange |
| 2011/0106003 A1 | 5/2011 | Childers |
| 2011/0130666 A1 | 6/2011 | Dong |
| 2011/0137136 A1 | 6/2011 | Kotanko |
| 2011/0141116 A1 | 6/2011 | Dalesch |
| 2011/0144570 A1 | 6/2011 | Childers |
| 2011/0184340 A1 | 7/2011 | Tan |
| 2011/0208105 A1 | 8/2011 | Brandl |
| 2011/0272337 A1 | 11/2011 | Palmer |
| 2011/0301447 A1 | 12/2011 | Park |
| 2011/0301472 A1 | 12/2011 | Grober |
| 2012/0016228 A1 | 1/2012 | Kroh |
| 2012/0083729 A1 | 4/2012 | Childers |
| 2012/0085707 A1 | 4/2012 | Beiriger |
| 2012/0115248 A1 | 5/2012 | Ansyln |
| 2012/0135396 A1 | 5/2012 | McDevitt |
| 2012/0181230 A1 | 7/2012 | Kloeffel |
| 2012/0220528 A1 | 8/2012 | VanAntwerp |
| 2012/0258545 A1 | 10/2012 | Ash |
| 2012/0258546 A1 | 10/2012 | Marran |
| 2012/0259276 A1 | 10/2012 | Childers |
| 2012/0273354 A1 | 11/2012 | Orhan et al. |
| 2012/0273415 A1 | 11/2012 | Gerber |
| 2012/0273420 A1 | 11/2012 | Gerber |
| 2012/0277546 A1 | 11/2012 | Soykan |
| 2012/0277551 A1 | 11/2012 | Gerber |
| 2012/0277552 A1 | 11/2012 | Gerber |
| 2012/0277604 A1 | 11/2012 | Gerber |
| 2012/0277650 A1 | 11/2012 | Gerber |
| 2012/0277655 A1 | 11/2012 | Gerber |
| 2012/0277722 A1 | 11/2012 | Gerber |
| 2012/0283581 A1 | 11/2012 | Olde et al. |
| 2012/0303079 A1 | 11/2012 | Mahajan |
| 2013/0037465 A1 | 2/2013 | Heyes |
| 2013/0062265 A1 | 3/2013 | Balschat |
| 2013/0116578 A1 | 5/2013 | An |
| 2013/0168316 A1 | 7/2013 | Noguchi |
| 2013/0193073 A1 | 8/2013 | Hogard |
| 2013/0199998 A1 | 8/2013 | Kelly |
| 2013/0211730 A1 | 8/2013 | Wolff |
| 2013/0213890 A1 | 8/2013 | Kelly |
| 2013/0228517 A1 | 9/2013 | Roger |
| 2013/0231607 A1 | 9/2013 | Roger |
| 2013/0248426 A1 | 9/2013 | Pouchoulin |
| 2013/0274642 A1 | 10/2013 | Soykan |
| 2013/0324915 A1 | 12/2013 | (Krensky)Britton |
| 2013/0330208 A1 | 12/2013 | Ly |
| 2013/0331774 A1 | 12/2013 | Farrell |
| 2014/0018727 A1 | 1/2014 | Burbank |
| 2014/0018728 A1 | 1/2014 | Plahey |
| 2014/0042092 A1 | 2/2014 | Akonur |
| 2014/0065950 A1 | 3/2014 | Mendelsohn |
| 2014/0088442 A1 | 3/2014 | Soykan |
| 2014/0110340 A1 | 4/2014 | White |
| 2014/0110341 A1 | 4/2014 | White |
| 2014/0158538 A1 | 6/2014 | Collier |
| 2014/0158588 A1 | 6/2014 | Pudil |
| 2014/0158623 A1 | 6/2014 | Pudil |
| 2014/0190876 A1 | 7/2014 | Meyer |
| 2014/0216250 A1 | 8/2014 | Meyer |
| 2014/0217028 A1 | 8/2014 | Pudil |
| 2014/0217029 A1 | 8/2014 | Meyer |
| 2014/0217030 A1 | 8/2014 | Meyer |
| 2014/0220699 A1 | 8/2014 | Pudil |
| 2014/0314625 A1 | 10/2014 | Clift |
| 2015/0032023 A1 | 1/2015 | Soykan |
| 2015/0080682 A1 | 3/2015 | Gerber |
| 2015/0088047 A1 | 3/2015 | Gerber |
| 2015/0144539 A1 | 5/2015 | Pudil |
| 2015/0148697 A1 | 5/2015 | Burnes |
| 2015/0149096 A1 | 5/2015 | Soykan |
| 2015/0250427 A1 | 9/2015 | Soykan |

(56) References Cited

U.S. PATENT DOCUMENTS

| | | |
|---|---|---|
| 2015/0343126 A1 | 12/2015 | Merchant |
| 2015/0352269 A1 | 12/2015 | Gerber |
| 2015/0367054 A1 | 12/2015 | Gerber |
| 2016/0023467 A1 | 2/2016 | Smith |
| 2016/0206801 A1 | 7/2016 | Gerber |
| 2016/0331884 A1 | 11/2016 | Sigg |
| 2019/0134289 A1* | 5/2019 | Pudil .................. A61M 1/1607 |

FOREIGN PATENT DOCUMENTS

| | | |
|---|---|---|
| EP | 0272414 | 10/1991 |
| EP | 0330892 | 7/1994 |
| EP | 1085295 | 11/2001 |
| EP | 1281351 | 2/2003 |
| EP | 2308526 | 10/2003 |
| EP | 1364666 A1 | 11/2003 |
| EP | 0906768 B1 | 2/2004 |
| EP | 1691863 | 4/2005 |
| EP | 2116269 | 2/2008 |
| EP | 1450879 | 10/2008 |
| EP | 1514562 | 4/2009 |
| EP | 2219703 | 5/2009 |
| EP | 1592494 B1 | 6/2009 |
| EP | 2398529 | 11/2010 |
| EP | 2100553 | 8/2011 |
| EP | 1345856 B1 | 3/2013 |
| EP | 2344220 B1 | 4/2013 |
| EP | 1351756 | 7/2013 |
| EP | 2190498 | 7/2013 |
| EP | 1582226 | 1/2016 |
| JP | S63-143077 | 11/1987 |
| JP | 2002533170 | 10/2002 |
| JP | 2003235965 | 8/2003 |
| JP | 2005-533573 | 11/2005 |
| WO | 1995003839 | 2/1995 |
| WO | WO 1998054563 | 12/1998 |
| WO | 0057935 | 10/2000 |
| WO | WO2000057935 A1 | 10/2000 |
| WO | 2000066197 | 11/2000 |
| WO | 200170307 A1 | 9/2001 |
| WO | 2001085295 A2 | 9/2001 |
| WO | 2002013691 | 2/2002 |
| WO | 2003043680 | 5/2003 |
| WO | 2003051422 A2 | 6/2003 |
| WO | 2004008826 | 1/2004 |
| WO | 2004009156 | 1/2004 |
| WO | 2004009158 | 1/2004 |
| WO | 2004030716 A2 | 4/2004 |
| WO | 2004030717 A2 | 4/2004 |
| WO | 2004064616 A2 | 8/2004 |
| WO | 2005033701 | 4/2005 |
| WO | 2005061026 | 7/2005 |
| WO | 2005123230 A2 | 12/2005 |
| WO | 2006011009 | 2/2006 |
| WO | 2006017446 | 2/2006 |
| WO | 2007038347 | 4/2007 |
| WO | 2007089855 A2 | 8/2007 |
| WO | 2008037410 | 4/2008 |
| WO | 2009026603 | 12/2008 |
| WO | 2009024566 | 2/2009 |
| WO | 2009061608 | 5/2009 |
| WO | 2009094184 | 7/2009 |
| WO | 2010024963 | 3/2010 |
| WO | 2010028860 | 3/2010 |
| WO | 2010033314 | 3/2010 |
| WO | 2010033699 | 3/2010 |
| WO | 2010077851 | 7/2010 |
| WO | 2010096659 | 10/2010 |
| WO | 2010121820 | 10/2010 |
| WO | 2011025705 A1 | 3/2011 |
| WO | 2011026645 | 3/2011 |
| WO | WO 2011/132046 | 10/2011 |
| WO | 2011137693 | 11/2011 |
| WO | WO2011161056 | 12/2011 |
| WO | 2012042323 | 4/2012 |
| WO | 2012050781 | 4/2012 |
| WO | 2012051996 | 4/2012 |
| WO | 2012073420 | 7/2012 |
| WO | 2012148781 | 11/2012 |
| WO | 2012148786 | 11/2012 |
| WO | 2012148787 A1 | 11/2012 |
| WO | 2012148789 | 11/2012 |
| WO | 2012162515 A2 | 11/2012 |
| WO | WO2012148788 A1 | 11/2012 |
| WO | WO 20120148784 | 11/2012 |
| WO | 2012172398 | 12/2012 |
| WO | 2013019179 A1 | 2/2013 |
| WO | 2013019994 A2 | 2/2013 |
| WO | 2013025844 | 2/2013 |
| WO | 2013028809 A3 | 2/2013 |
| WO | 2013101292 | 7/2013 |
| WO | 2013103607 A1 | 7/2013 |
| WO | 2013103906 | 7/2013 |
| WO | 2013110906 | 8/2013 |
| WO | 2013110919 | 8/2013 |
| WO | 2013114063 A1 | 8/2013 |
| WO | 2013121162 A1 | 8/2013 |
| WO | 2013140346 | 9/2013 |
| WO | 2013141896 | 9/2013 |
| WO | 14066254 | 5/2014 |
| WO | 14066255 | 5/2014 |
| WO | 14077082 | 5/2014 |
| WO | 2014121167 | 8/2014 |
| WO | 2014121169 | 8/2014 |
| WO | 2014211162 | 8/2014 |
| WO | 2014211163 | 8/2014 |
| WO | WO 20140121161 | 8/2014 |
| WO | WO2012081221 A1 | 6/2015 |
| WO | WO 20150159280 | 10/2015 |

OTHER PUBLICATIONS

[NPL10] Wheaton, et al., Dowex Ion Exchange Resins-Fundamentals of Ion Exchange; Jun. 2000, pp. 1-9. http://www.dow.com/scripts/litorder.asp?filepath=liquidseps/pdfs/noreg/177-01837.pdf.

[NPL111] Zhong, et. al., Miniature urea sensor based on H(+)-ion sensitive field effect transistor and its application in clinical analysis, Chin. J. Biotechnol., 1992, 57-65. 8(1).

[NPL121] Roberts M, The regenerative dialysis (REDY) sorbent system. Nephrology, 1998, 275-278:4.

[NPL142] Hemametrics, Crit-Line Hematocrit Accuracy, 2003, 1-5, vol. 1, Tech Note No. 11 (Rev. D).

[NPL144] Weissman, S., et al., Hydroxyurea-induced hepatitis in human immunodeficiency virus-positive patients. Clin. Infec. Dis, (Jul. 29, 1999): 223-224.

[NPL14] Foley, et al., Long Interdialytic Interval and Martality among Patients Receiving Hemodialysis, N Engl Jrnl Med. 2011:365(12):1099-1107.

[NPL169] Wang, Fundamentals of intrathoracic impedance monitoring in heart failure, Am. J. Cardiology, 2007, 3G-10G: Suppl.

[NPL176] Bleyer, et al., Sudden and cardiac death rated in hemodialysis patients, Kidney International. 1999, 1553-1559: 55.

[NPL205] Culleton, BR et al. Effect of Frequent Nocturnal Hemodialysis vs. Conventional Hemodialysis on Left Ventricular Mass and Quality of Life. 2007 Journal of the American Medical Association 298 (11), 1291-1299.

[NPL230] Redfield, et. al., Restoration of renal response to atrial natriuretic factor in experimental low-output heat failure, Am. J. Physiol., Oct. 1, 1989, R917-923:257.

[NPL231] Rogoza, et. al., Validation of A&D UA-767 device for the self-measurement of blood pressure, Blood Pressure Monitoring, 2000, 227-231, 5(4).

[NPL234] Lima, et. al., An electrochemical sensor based on nanostructure hollandite-type manganese oxide for detection of potassium ion, Sensors, Aug. 24, 2009, 6613-8625, 9.

[NPL235] Maclean, et. al., Effects of hindlimb contraction on pressor and muscle interstitial metabolite responses in the cat, J. App. Physiol., 1998, 1583-1592, 85(4).

(56) References Cited

OTHER PUBLICATIONS

[NPL26] Overgaard, et. al., Activity-induced recovery of excitability in K+-depressed rat soleus muscle, Am. J. P 280: R48-R55, Jan. 1, 2001.
[NPL27] Overgaard et. al., Relations between excitability and contractility in rate soleusmuscle: role of the NA+-K+ pump and NA+-K-S gradients. Journal of Physiology, 1999, 215-225, 518(1).
[NPL306] Coast, et al. 1990, An approach to Cardiac Arrhythmia analysis Using Hidden Markov Models, IEEE Transactions On Biomedical Engineering. 1990, 37(9):826-835.
[NPL309] Weiner, et. al., Article: Cardiac Function and Cardiovascular Disease in Chronic Kidney Disease, Book: Primer on Kidney Diseases (Author: Greenberg, et al.), 2009,499-505, 5th Ed., Saunders Elsevier, Philadelphia, PA.
[NPL322] Velasco, Optimal Fluid Control can Normalize Cardiovascular Risk Markers and Limit Left Ventricular Hypertrophy in Thrice Weekly Dialysis Patients, Hemodialysis Intenational, 16:465-472, 2012.
[NPL323] Whitman, CKD and Sudden Cardiac Death: Epidemiology, Mechanisms, and Therapeutic Approaches, J Am Soc Nephrol, 23:1929-1939, 2012.
[NPL324] Hall, Hospitalization for Congestive Heart Failure: United States, 2000-2010, NCHS Data Brief, No. 108, Oct. 2012.
[NPL325] Albert, Fluid Management Strategies in Heart Failure, Critical Care Nurse, 32:20-32, 2012.
[NPL328] Genovesi, et al., Nephrology, Dialysis, Transplantation 2009; 24(8):2529-2536.
[NPL32] Secemsky, et al., High prevalence of cardiac autonomic dysfunction and T-wave alternans in dialysis patients. Heart Rhythm, Apr. 2011, 592-598 : vol. 8, No. 4.
[NPL35] Wei, et. al., Fullerene-cryptand coated piezoelectric crystal urea sensor based on urease, Analytica Chimica Acta, 2001,77-85:437.
[NPL376] Gambro AK 96 Dialysis Machine Operators Manual, Dec. 2012. p. 1-140.
[NPL376] Gambro AK 96 Dialysis Machine Operators Manual, Dec. 2012. p. 141-280.
[NPL376] Gambro AK 96 Dialysis Machine Operators Manual, Dec. 2012. p. 281-420.
[NPL376] Gambro AK 96 Dialysis Machine Operators Manual, Dec. 2012. p. 421-534.
[NPL383] Leifer et al., A Study on the Temperature Variation of Rise Velocity for Large Clean Bubbles, J. Atmospheric & Oceanic Tech., vol. 17, pp. 1392-1402, Oct. 2000.
[NPL384] Talaia, Terminal Velocity of a Bubble Rise in a Liquid Column, World Acad. of Sci., Engineering & Tech., vol. 28, pp. 264-268, Published Jan. 1, 2007.
[NPL386] The FHN Trial Group. In-Center. Hemodialysis Six Times per Week versus Three Times per Week, New England Journal of Medicine, 2010 Abstract.
[NPL46] Siegenthaler, et al., Pulmonary fluid status monitoring with intrathoracic impedance, Journal of Clinical Monitoring and Computing, 24:449-451, published Jan. 12, 2011.
[NPL494] John Wm Agar: Review: Understanding sorbent dialysis systems, Nephrology, vol. 15, No. 4, Jun. 1, 2010, pp. 406-411.
[NPL632] Lakerveld et al, Primary prevention of diabetes mellitus type 2 and cardiovascular diseases using a cognitive behavior program aimed at lifestyle changes in people at risk: Design of a randomized controlled trial, 2008, BMC Endocrine Disorders, 8(6): 1-19.
[NPL633] Gordhandas et al., Real-Time Extraction and Analysis of Key Morphological Features in the Electrocardiogram, for Data Compression and Clinical Decision Support, 2004, Computational Physiology, pp. 15-18.
[NPL90] Nedelkov, et. al., Design of buffer exchange surfaces and sensor chips for biosensor chip mass spectrometry, Proteomics, 2002, 441-446, 2(4).
[NPL] Green et. al., Sudden Cardiac Death in Hemodialysis Patients: an In-Depth Review , Am J Kidney Dis 57(6)921:929; published Apr. 18, 2011.
[NPL] Rajan et al. Generalized Feature Extraction for Time-Varying Autoregressive Models, IEEE Transacion Signal Processing vol. 44, No. 10; published Oct. 1, 1996.
Laurent, Jeanpierre, "Continuous Monitoring of Dynamic Systems: Application to Monitoring of Dialyzed Patients" Oct. 30, 2004, received from internet: http://laurent.jeanpierre1.free.fr/recherche/papiers/aista2004.pdf.
Wollenstein, et al, "Colorimetric gas sensors for the detection of ammonia, nitrogen dioxide, and carbon monoxide: current status and research trends", Sensor and Test Conference 2011, Jan. 2, 2011, pp. 562-567.

\* cited by examiner

SODIUM AND BICARBONATE CONTROL

FIELD

Systems, components, and methods are provided for controlling the sodium and bicarbonate concentrations in a dialysate. The systems, components, and methods can use conductivity sensors to control the addition of water and bicarbonate to accurately control the final concentrations of both sodium and bicarbonate.

BACKGROUND

Sorbent-based recirculating dialysis systems often remove urea from spent dialysate by first converting the urea to carbon dioxide and ammonium ions, and then removing the ammonium ions from solution. The formation of carbon dioxide, which exists in equilibrium with bicarbonate, makes control over the bicarbonate concentration of the dialysate difficult. In a typical regenerative dialysis sorbent system sodium and bicarbonate are partially removed or generated across a sorbent cartridge, usually to unpredictable levels. Therefore, the amount of sodium and bicarbonate to add to the dialysate to achieve a desired prescription level is unpredictable and can lead to inaccurate levels.

Hence, there is a need for systems and methods for controlling the bicarbonate and sodium concentrations in the dialysate of a sorbent-based dialysis system. The need extends to systems and methods that allow for accurate control of sodium and bicarbonate without the need to directly measure and adjust the bicarbonate concentration prior to the dialysate reaching the dialyzer. There is a further need for systems and methods that can control the bicarbonate and sodium concentration throughout an entire dialysis session, even as the pH and composition of the solution leaving the sorbent cartridge changes.

SUMMARY OF THE INVENTION

The problem to be solved is controlling bicarbonate and sodium concentration in a dialysate throughout a dialysis session. The solution is to use a two-phase control, removing substantially all of the bicarbonate from solution during a first low pH phase, and then using information obtained during the first phase to control the bicarbonate and sodium concentration in a second, higher pH phase.

The first aspect relates to a system. In any embodiment, the system can include a dialysate flow path; the dialysate flow path fluidly connectable to a dialysate inlet of a dialyzer and a dialysate outlet of the dialyzer; a sorbent cartridge in the dialysate flow path; a degasser in the dialysate flow path downstream of the sorbent cartridge; a bicarbonate source fluidly connected to the dialysate flow path; a water source fluidly connected to the dialysate flow path; a first conductivity sensor downstream of the sorbent cartridge; and a control system; the control system programmed to determine a pH of a fluid exiting the sorbent cartridge; wherein: while pH of the fluid exiting the sorbent cartridge is below a preset pH, the control system is programmed to control a sodium concentration in the fluid based on a sodium prescription and a conductivity measured by the first conductivity sensor; and to control a bicarbonate concentration in the fluid based on a bicarbonate prescription.

In any embodiment, the preset pH can be about 4.8.

In any embodiment, the sorbent cartridge can include zirconium phosphate at a low pH.

In any embodiment, while the pH of the fluid exiting the sorbent cartridge is below the preset pH, the control system can be programmed to control the sodium concentration in the fluid by adding water from a water source upstream of the sorbent cartridge to a target post-sorbent conductivity setpoint.

In any embodiment, while the pH of the fluid exiting the sorbent cartridge is below the preset pH, the control system can be programmed to control the bicarbonate concentration in the fluid by adding bicarbonate from a bicarbonate source downstream of the sorbent cartridge to a target conductivity delta between a conductivity sensor after the sorbent cartridge and a conductivity sensor after the bicarbonate source.

In any embodiment, the system can include a hydrochloric acid source fluidly connected to the dialysate flow path upstream of the sorbent cartridge.

In any embodiment, the system can include at least one infusate source downstream of the sorbent cartridge.

In any embodiment, the control system can be programmed to detect release of sulfate ions from the sorbent cartridge.

In any embodiment, wherein the control system can be programmed to dilute the fluid during the release of sulfate ions.

In any embodiment, while the pH of the fluid exiting the sorbent cartridge is above a preset pH, the control system can be programmed to control the sodium concentration in the fluid by adding water from a water source upstream of the sorbent cartridge to a target pre-sorbent conductivity setpoint.

In any embodiment, the pre-sorbent conductivity can be measured with a second conductivity sensor upstream of the sorbent cartridge.

In any embodiment, the target pre-sorbent conductivity setpoint can be a conductivity measured upstream of the sorbent cartridge while the pH is below the preset pH.

In any embodiment, while the pH of the fluid exiting the sorbent cartridge is above a preset pH, the control system can be programmed to control the bicarbonate concentration in the fluid by adding bicarbonate to reach a target post-bicarbonate conductivity setpoint.

In any embodiment, the target post-bicarbonate conductivity setpoint can be based on the sodium and a bicarbonate prescription.

In any embodiment, the pH of the fluid exiting the sorbent cartridge can be measured with a pH sensor downstream of the sorbent cartridge.

In any embodiment, the pH of the fluid exiting the sorbent cartridge can be measured based on changes to a degasser output.

In any embodiment, the pH of the fluid exiting the sorbent cartridge can be measured based on a conductivity change across the sorbent cartridge measured by the first conductivity sensor and a second conductivity sensor upstream of the sorbent cartridge.

In any embodiment, the pH of the fluid exiting the sorbent cartridge can be measured based on a volume of the water added from the water source.

In any embodiment, the control system can be programmed to isolate the sorbent cartridge prior to determining the pH of the fluid exiting the sorbent cartridge.

The features disclosed as being part of the first aspect can be in the first aspect, either alone or in combination, or follow any arrangement or permutation of any one or more of the described elements. Similarly, any features disclosed as being part of the first aspect can be in a second aspect described below, either alone or in combination, or follow any arrangement or permutation of any one or more of the described elements.

The second aspect relates to a method. In any embodiment, the method can include determining a pH of a fluid exiting a sorbent cartridge of a sorbent dialysis system; and while pH of the fluid exiting the sorbent cartridge is below a preset pH, controlling a sodium concentration in the fluid based on a sodium prescription and a conductivity measured by a first conductivity sensor downstream of the sorbent cartridge; and controlling a bicarbonate concentration in the fluid based on a bicarbonate prescription.

In any embodiment, the preset pH can be about 4.8.

In any embodiment, the sorbent cartridge can include zirconium phosphate at a low pH.

In any embodiment, while the pH of the fluid exiting the sorbent cartridge is below a preset pH, the step of controlling the sodium concentration in the fluid can include adding water from a water source upstream of the sorbent cartridge to a target post-sorbent conductivity setpoint.

In any embodiment, while the pH of the fluid exiting the sorbent cartridge is below a preset pH, the step of controlling the bicarbonate concentration in the fluid can include adding bicarbonate from a bicarbonate source upstream of the sorbent cartridge and degasser to a target post-bicarbonate conductivity setpoint.

In any embodiment, the post-bicarbonate conductivity set point can be based on a conductivity increase between fluid downstream of the degasser and upstream of the bicarbonate source and fluid downstream of the bicarbonate source.

In any embodiment, the method can include the step of adding hydrochloric acid to the dialysate flow path upstream of the sorbent cartridge.

In any embodiment, while the pH of the fluid exiting the sorbent cartridge is above a preset pH, the method can include controlling the sodium concentration in the fluid by adding water from a water source upstream of the sorbent cartridge to a target pre-sorbent conductivity setpoint.

In any embodiment, target pre-sorbent conductivity setpoint can be a pre-sorbent conductivity measured while the pH is below the preset pH.

In any embodiment, while the pH of the fluid exiting the sorbent cartridge is above a preset pH, the step of controlling the bicarbonate concentration in the fluid can include adding bicarbonate to reach a post-bicarbonate conductivity setpoint.

In any embodiment, the post-bicarbonate conductivity setpoint can be based on the sodium and a bicarbonate prescription.

The features disclosed as being part of the second aspect can be in the second aspect, either alone or in combination, or follow any arrangement or permutation of any one or more of the described elements. Similarly, any features disclosed as being part of the second aspect can be in the first aspect, either alone or in combination, or follow any arrangement or permutation of any one or more of the described elements.

DETAILED DESCRIPTION

Figure 1:
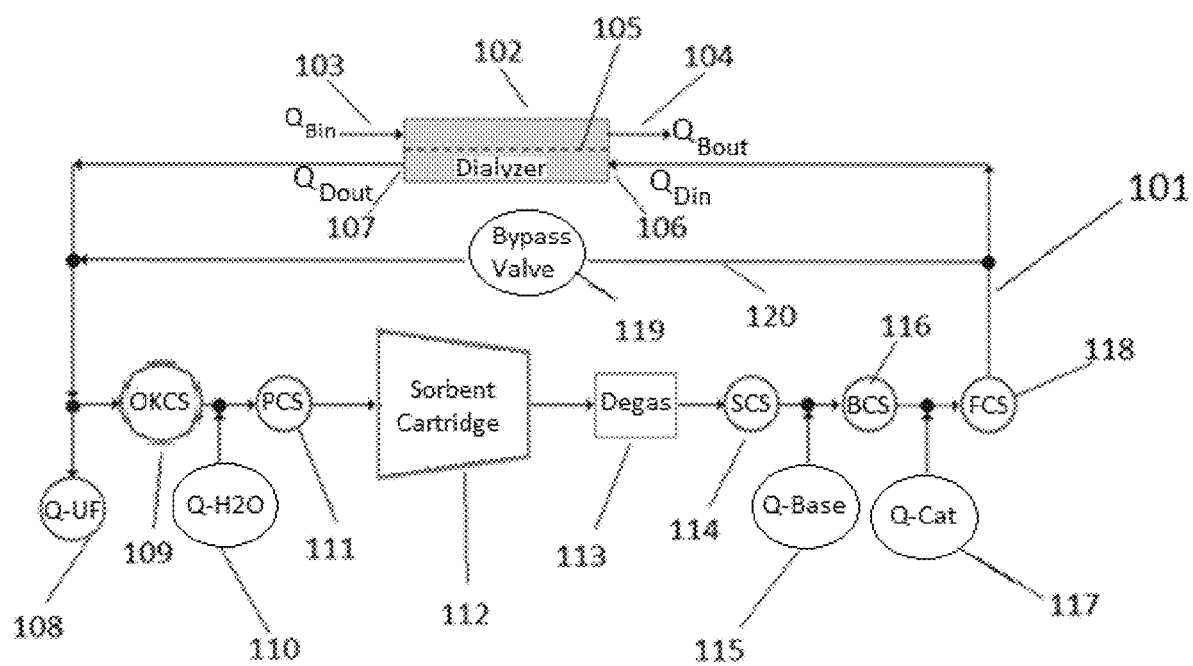
FIG. 1 is a simplified drawing of a dialysis system.

Unless defined otherwise, all technical and scientific terms used have the same meaning as commonly understood by one of ordinary skill in the art.

The articles "a" and "an" are used to refer to one to over one (i.e., to at least one) of the grammatical object of the article. For example, "an element" means one element or over one element.

The term "adding," to "add," or "addition" refers to pumping additional fluid into an existing fluid or into a component or system.

The term "bicarbonate" refers to $HCO_3^-$ ions, as well as any species existing in equilibrium with bicarbonate ions, including carbonate ions and carbon dioxide.

The term "bicarbonate concentration" refers to an amount of bicarbonate dissolved in a solvent per a given amount of solvent.

A "bicarbonate prescription" is an intended bicarbonate concentration in the dialysate or blood.

The term "bicarbonate source" can refer to a source of bicarbonate ions or bicarbonate predecessors. The bicarbonate can be in acid or basic form, and can include substances that react to form bicarbonate when used in a dialysis system.

The term "blood flow rate" refers to a volume of blood moving through a system per unit of time.

The term "comprising" includes, but is not limited to, whatever follows the word "comprising." Use of the term indicates the listed elements are required or mandatory but that other elements are optional and may be present.

The term "conductivity" refers to the inverse of the electrical resistance of a fluid.

The term "conductivity change across the sorbent cartridge" refers to a difference in conductivity of a fluid prior to the fluid entering a sorbent cartridge and after the fluid exits the sorbent cartridge.

The term "conductivity increase" refers to a positive change in conductivity of a fluid as the fluid moves through a system.

The term "conductivity sensor" refers to any component capable of measuring the electrical conductance or the electrical resistance of a fluid.

The term "consisting of" includes and is limited to whatever follows the phrase "consisting of." The phrase indicates the limited elements are required or mandatory and that no other elements may be present.

The term "consisting essentially of" includes whatever follows the term "consisting essentially of" and additional elements, structures, acts, or features that do not affect the basic operation of the apparatus, structure or method described.

The terms "control," "controlling," or "controls" can refer to the ability of one component to direct the actions of a second component.

A "control system" is a device which monitors and affects the operational conditions of a given system. The operational conditions are typically referred to as output variables of the system wherein the output variables can be affected by adjusting certain input variables.

A "degasser" refers to any device, component, or system that can be used to remove one or more gases from a fluid.

The term "degasser output" can refer to an amount of gas removed from a fluid by a degasser, or to the composition of gases removed from the fluid.

The term "detect" refers to ascertaining a state of a system or component.

The terms "determining," "determines," and the like, generally refer to, in the broadest reasonable interpretation, any process or method for obtaining or coming to a decision, value, number, or finding, for any one or more value, output, parameter, or variable, by any means applicable to the relevant parameter being determined.

The term "dialysate" refers to any mixture that provides for passing solutes of any type through a membrane of any type. Typically, a dialysate contains a concentration of solutes to exchange solutes across a gradient to and from the dialysate during dialysis therapy.

The term "dialysate flow path" refers to a pathway through which dialysate travels during dialysis therapy.

The term "dialysate flow rate" refers to a volume of dialysate moving through a system per unit of time.

The term "dialysate inlet" refers to an opening or conduit through which dialysate can enter a component.

The term "dialysate outlet" refers to an opening or conduit through which dialysate can exit a component.

The term "dialyzer" can refer to a cartridge or container with two flow paths separated by semi-permeable membranes. One flow path can be for blood and one flow path can be for dialysate. The membranes can be in hollow fibers, flat sheets, or spiral wound or other conventional forms known to those of skill in the art. Membranes can be selected from any one or combination of materials: polysulfone, polyethersulfone, poly (methyl methacrylate), modified cellulose, or other materials known to those skilled in the art.

The term "dialyzer size" refers to the amount of fluid that can be contained within a dialyzer.

The term "dilute" means to lower a concentration of one or more solutes in solution.

The term "downstream" refers to a position of a first component in a flow path relative to a second component wherein fluid, gas, or combinations thereof, will pass by the second component prior to the first component during normal operation. The first component can be said to be "downstream" of the second component, while the second component is "upstream" of the first component.

The term "estimate" can refer to an approximation of a value for a particular parameter.

The terms "exit" or "exiting" refer to a fluid leaving a container or component.

The term "fluidly connectable" refers to the ability to provide passage of fluid, gas, or combinations thereof, from one point to another point. The ability to provide such passage can be any mechanical connection, fastening, or forming between two points to permit the flow of fluid, gas, or combinations thereof. The two points can be within or between any one or more of compartments, modules, systems, components, and rechargers, all of any type. Notably, the components that are fluidly connectable, need not be a part of a structure. For example, an outlet "fluidly connectable" to a pump does not require the pump, but merely that the outlet has the features necessary for fluid connection to the pump.

The term "fluidly connected" refers to a particular state or configuration of one or more components such that fluid, gas, or combination thereof, can flow from one point to another point. The connection state can also include an optional unconnected state or configuration, such that the two points are disconnected from each other to discontinue flow. It will be further understood that the two "fluidly connectable" points, as defined above, can form a "fluidly connected" state. The two points can be within or between any one or more of compartments, modules, systems, components, all of any type.

The term "hydrochloric acid source" refers to any source from which hydrochloric acid, or HCl, can be obtained.

The term "infusate source" refers to one or more sources of cations, such as potassium, calcium, or magnesium cations, for addition to a dialysate.

The term "isolate" refers to configuring a system such that a given component is not in fluid communication with a second given component.

The term "low pH" refers to a pH low enough that will result in substantially all bicarbonate being converted to carbon dioxide.

The term "measuring" or "to measure" can refer to determining any parameter or variable. The parameter or variable can relate to any state or value of a system, component, fluid, gas, or mixtures of one or more gases or fluids.

The term "patient bicarbonate level" refers to the bicarbonate concentration in the blood of a patient.

The term "patient size" refers to the mass or weight of a patient.

The term "patient urea level" refers to the urea concentration in the blood of a patient.

"pH" is a value equal to the negative log of the $H^+$ ion concentration in a fluid.

The term "pH sensor" refers to any sensor or set of sensors that can be used to determine the pH of a fluid.

The term "preset" refers to a value of a parameter or state of a component or system that is determined in advance of a dialysis session.

The term "programmed," when referring to a processor, can mean a series of instructions that cause a processor to perform certain steps.

The term "release" refers to one or more substances being added by a component to a fluid.

The term "sodium" refers to Na ions in solution.

The term "sodium concentration" refers to an amount of sodium ions dissolved in a given amount of solvent.

A "sodium prescription" is an intended sodium concentration in a dialysate or blood.

The terms "sorbent cartridge" and "sorbent container" can refer to a cartridge containing one or more sorbent materials for removing specific solutes from solution, such as urea. The term "sorbent cartridge" does not require the contents in the cartridge be sorbent based, and the contents of the sorbent cartridge can be any contents that can remove waste products from a dialysate. The sorbent cartridge may include any suitable amount of one or more sorbent materials. In certain instances, the term "sorbent cartridge" can refer to a cartridge which includes one or more sorbent materials in addition to one or more other materials capable of removing waste products from dialysate. "Sorbent cartridge" can include configurations where at least some materials in the cartridge do not act by mechanisms of adsorption or absorption. In any embodiment, a system may include a number of separate cartridges which can be physically separated or interconnected wherein such cartridges can be optionally detached and reattached as desired. The term "sulfate ions" refers to $SO_4^{2-}$ in acid or basic form, or with any counter ions.

The term "target post-bicarbonate conductivity setpoint" refers to a conductivity value, measured after bicarbonate has been added to a fluid, that will result in an intended prescription for a dialysate.

The term "target post-sorbent conductivity setpoint" refers to a conductivity value, measured after a fluid has passed through a sorbent cartridge, that will result in an intended prescription for a dialysate.

The term "target pre-sorbent conductivity setpoint" refers to a conductivity value, measured before a fluid has passed through a sorbent cartridge, that will result in an intended prescription for a dialysate.

The term "ultrafiltration rate" refers to a volume of fluid removed from the blood of a patient per unit of time.

The term "upstream" refers to a position of a first component in a flow path relative to a second component wherein fluid, gas, or combinations thereof, will pass by the first component prior to the second component during normal operation. The first component can be said to be "upstream" of the second component, while the second component is "downstream" of the first component.

A "water source" can be any fluid source from which water can be obtained. The source can be any type of reservoir, fluid line, or receptacle. The water from the water source can be water with or without any dissolved solutes, including one or more buffer or ions.

"Zirconium phosphate" is a sorbent material that removes cations from a fluid, exchanging the removed cations for different cations.

Sodium and Bicarbonate Control

FIG. 1 is a simplified diagram of a sorbent-based dialysis system. A dialyzer 102 can be fluidly connected to an extracorporeal flow path (not shown) and fluidly connectable to a dialysate flow path 101. Blood from a patient can enter the dialyzer 102 through blood inlet 103 and exit the dialyzer 102 through blood outlet 104. At the same time, dialysate can enter the dialyzer 102 through dialysate inlet 106 and exit through dialysate outlet 107. The dialysate and blood are separated in the dialyzer 102 by semi-permeable membrane 105. Solutes and fluid can pass between the blood and the dialysate through semi-permeable membrane 105.

After exiting the dialyzer 102, the dialysate can be pumped through dialysate flow path 101. One or more pumps (not shown) can provide the driving force necessary to control the movement of dialysate through the dialysate flow path 101. A portion of the dialysate can be drawn off as ultrafiltrate by ultrafiltration system 108. If necessary to control sodium concentration, water can be added to the dialysate from water source 110. The used dialysate can be pumped through sorbent cartridge 112 to regenerate the dialysate.

The sorbent cartridge 112 can include one or more sorbent materials to remove solutes from the dialysate, allowing the dialysate to be reused. In certain embodiments, the sorbent cartridge 112 can include activated carbon to remove creatinine, glucose, uric acid, β2-microglobulin and other non-ionic toxins, except urea, from the dialysate. The sorbent cartridge can also include urease, which converts urea to ammonium ions and carbon dioxide. Zirconium oxide in the sorbent cartridge 112 can remove phosphate, fluoride, and other anions from the dialysate. Zirconium phosphate in sorbent cartridge 112 can remove the ammonium ions generated from the breakdown of urea by the urease, as well as potassium, calcium, and magnesium cations. The cations removed by the zirconium phosphate can be exchanged for sodium and hydrogen ions.

Carbon dioxide present in the dialysate exiting the sorbent cartridge 112 can be removed by degasser 113 located downstream of the sorbent cartridge 112. Bicarbonate can be added to the dialysate from bicarbonate source 115 and cations, such as potassium, magnesium, and calcium, can be added back into the dialysate from cation infusate source 117. In certain embodiments, bypass line 120 and bypass valve 119 can be included to bypass either the dialyzer 102 or the sorbent cartridge 112.

One of skill in the art will understand that the system illustrated in FIG. 1 is a simplified system for illustrative purposes only. Additional components can be included. For example, additional pumps and valves can be included for operation of the degassing system, as well as control over ultrafiltration and addition of water, bicarbonate, and cation infusate. The pumps and valves can be operated by a control system (not shown). The control system can be programmed to receive data from sensors at various positions in the dialysate flow path 101, to determine any parameters or system state based on the received data, and to control the components of the dialysis system. For example, conductivity sensor 109 can be included to determine the conductivity of the dialysate exiting the dialyzer 102. Conductivity sensor 111 can be included to determine the conductivity of dialysate after addition of water and prior to reaching the sorbent cartridge 112. Conductivity sensor 114 can be included to measure the conductivity of the dialysate after the degasser and prior to addition of bicarbonate solution. Conductivity sensor 116 can be used to measure the conductivity of the dialysate after addition of bicarbonate and prior to addition of cation infusate. Conductivity sensor 118 can be included to measure the conductivity after the addition of the cation infusate to ensure the final dialysate has a proper composition prior to reaching the dialyzer 102. Additional sensors (not shown), such as temperature sensors, pressure sensors, pH sensors, or any other sensors can be included.

Figure 2:
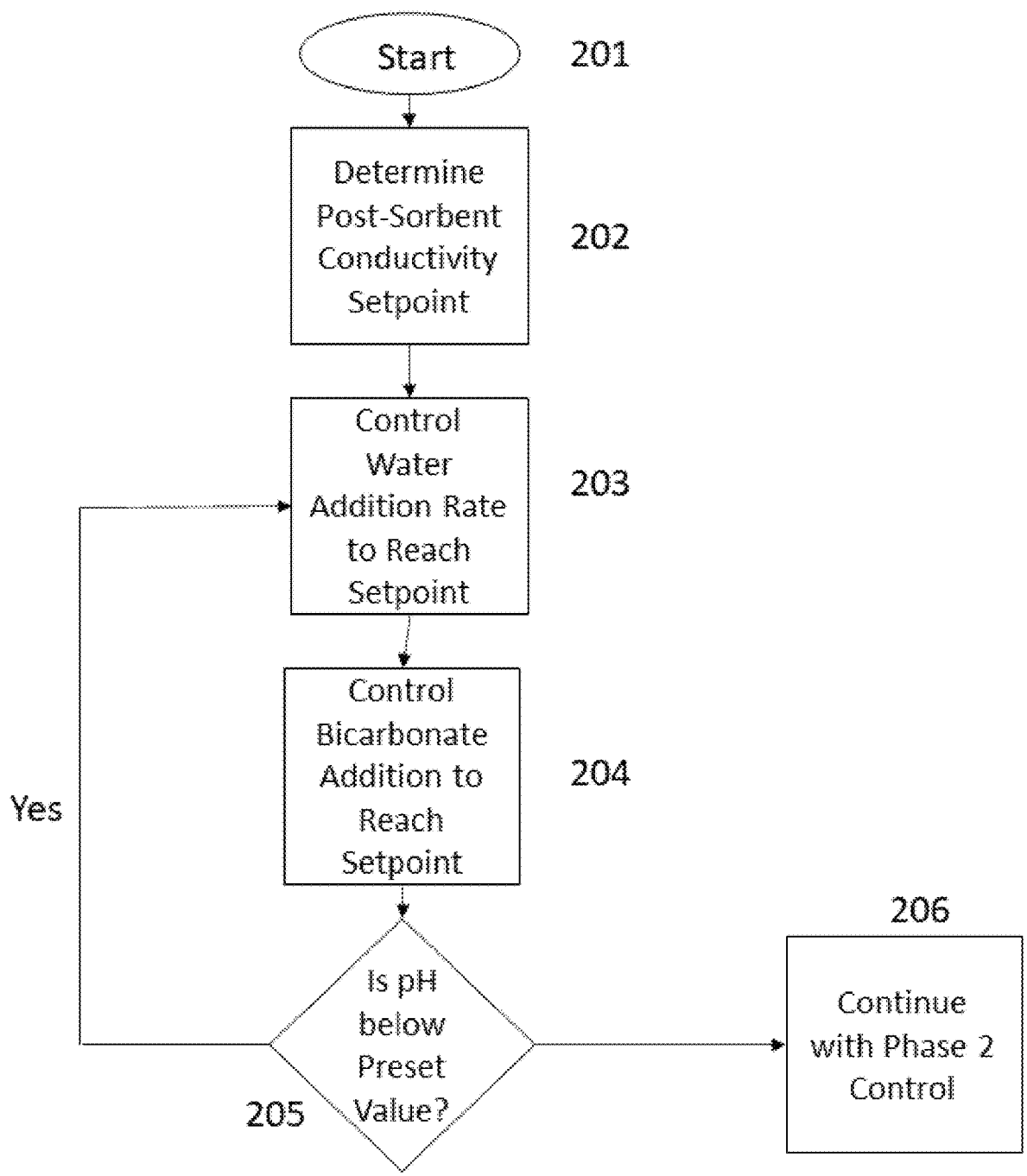
FIG. 2 is a flow chart showing a method of controlling sodium and bicarbonate during a low-pH phase.

In certain embodiments, the system can control the sodium and bicarbonate concentrations in the dialysate using a two-phase approach. FIG. 2 is a flow chart showing control over the sodium and bicarbonate concentration during the first phase. In step 201, the process can begin. In the beginning of a dialysis session, the sorbent cartridge 112 can be a low-pH sorbent cartridge. The pH of the sorbent cartridge can be controlled by controlling the initial hydrogen to sodium ratio of the zirconium phosphate. A higher proportion of hydrogen ions will result in a lower pH of fluid exiting the sorbent cartridge.

When the sorbent cartridge effluent pH is below a preset pH, substantially all bicarbonate in the dialysate will be converted to carbon dioxide and subsequently removed by the degasser, effectively reducing the total CO2 or bicarbonate to a level approaching 0-mM and allowing control over both the sodium and bicarbonate concentration in the dialysate. In step 202, the system can determine a post-sorbent conductivity setpoint that will result in a desired sodium concentration. Knowing that the bicarbonate level is near zero allows an accurate conductivity value to be determined because the sorbent effluent will mainly depend on the concentration of sodium and chloride. The post-sorbent conductivity setpoint can be set based on both the sodium and bicarbonate prescriptions. For example, if a dialysate sodium of 140-mM and bicarbonate of 40-mM are desired, the sodium chloride level needed at sorbent outlet would be 100-mM and the conductivity set-point would correspond to the conductivity of a 100-mM sodium chloride solution. The remaining 40 mM of sodium will be added by addition of sodium bicarbonate after the dialysate passes through the degasser 113. Water from water source 110 can be added to the dialysate to dilute the dialysate if necessary to reach the post-sorbent conductivity setpoint in step 203. Although illustrated in FIG. 1 as upstream of the sorbent cartridge 112, the water source 110 can alternatively be positioned downstream of the sorbent cartridge 112.

The bicarbonate concentration of the dialysate is controlled in step 204. As described, during phase 1 control, the pH of the sorbent cartridge effluent is low enough to convert substantially all bicarbonate to carbon dioxide, which is removed by degasser 113. To accurately control bicarbonate concentration in the dialysate, sodium bicarbonate from bicarbonate source 115 can be added. The system can control the addition of bicarbonate to achieve a post-bicarbonate conductivity setpoint as measured by conductivity sensor 116. The post-bicarbonate conductivity setpoint can be a fixed value based on the sodium and bicarbonate prescription. Alternatively, the post-bicarbonate conductivity setpoint can be based on achieving a target conductivity delta between the post-degasser conductivity sensor 114 and the post-bicarbonate conductivity sensor 116. For example, a bicarbonate prescription of 40-mM would require the addition of 40-mM bicarbonate from the bicarbonate source, which corresponds to a certain conductivity increase between conductivity sensor 114 and 116. Therefore, the bicarbonate source can be added to achieve the desired conductivity increase at sensor 116 relative to sensor 114. After the bicarbonate is added to the dialysate, a cation infusate can be added to control the potassium, calcium, and magnesium concentrations. In certain embodiments, the cation infusate can also include sodium. In such embodiments, the post-sorbent conductivity set point can be adjusted to account for the additional sodium.

As described, the phase 1 control over sodium and bicarbonate can continue while the sorbent effluent pH is low enough to convert substantially all the bicarbonate to carbon dioxide. In step 205, the system can monitor the sorbent cartridge effluent pH, and determine whether the sorbent cartridge effluent pH is below a preset pH. If the sorbent cartridge effluent pH is below the preset pH, the method can continue in step 203, with control over both sodium and bicarbonate. If the pH exceeds the preset pH, some level of bicarbonate can remain in the dialysate after passing through the sorbent cartridge 112 and degasser 113. The system can then switch to a phase 2 control method in step 206. In certain embodiments, the preset pH for the sorbent cartridge effluent pH can be about 4.8, which will result in substantially all the bicarbonate being removed from the dialysate.

One of skill in the art will understand that several options for determining when to switch to phase 2 control can be used. Optionally, the system can use a pH sensor at the outlet of the sorbent cartridge to measure the effluent pH. Alternatively, the system can monitor the degasser output to determine changes in the sorbent effluent pH. As the pH rises, there will be less $CO_2$ to degas, and the degasser output will decrease. In certain embodiments, the system can detect the sorbent cartridge effluent pH state based on conductivity changes across the sorbent cartridge. As the pH of the sorbent cartridge increases, the bicarbonate concentration, and corresponding sodium concentration, increases, resulting in a smaller conductivity change across the sorbent cartridge. The system can also detect the sorbent cartridge effluent pH state based on changes in the water addition rate needed to maintain the sorbent outlet conductivity target during phase one control. As the pH rises and the sodium bicarbonate concentration increases, the sorbent outlet conductivity will increase and require an increase in water dilution to maintain the post-sorbent conductivity setpoint. Periodic isolation of the sorbent cartridge from the dialyzer and measurement of the above parameters can also be used to predict the sorbent cartridge pH state. Isolation of the dialyzer removes unknown contributions to the dialysate from the patient and results on a more accurate prediction of the pH state. To isolate the sorbent cartridge from the dialyzer, dialysate can be pumped through a bypass line, such as bypass line 120 in FIG. 1, recirculating the dialysate through the sorbent cartridge 112 without passing through the dialyzer 102. Refinement of the pH state determination using the described methods can be achieved by using more than one method listed, either to refine detection with a single-method or used together. Also, detection can be refined based on early conductivity changes across the dialyzer and/or across the sorbent cartridge. These early conductivity changes can be indicative of patient levels and used to further refine detection of the dialysate pH. In addition, integration of the conductivity change across the sorbent cartridge can be used as a measure of the cumulative bicarbonate exposure to the sorbent cartridge, and transition to phase two control can be done when the cumulative exposure reaches a preset value.

Alternatively, the detection of sorbent outlet pH can be determined based on the conductivity change across the sorbent cartridge normalized to the water dilution rate needed to achieve the target post-sorbent conductivity setpoint by using equation (1): $(SCS-PCS)/(1-Q-H_2O/Q_{Dout})$, wherein SCS is the conductivity measured by conductivity sensor 114, PCS is the conductivity measured by conductivity sensor, $Q-H_2O$ is the water addition rate from water source 110, and $Q_{Dout}$ is the dialysate flow rate at the dialyzer outlet 107. In addition, the SCS and PCS values used in equation (1) can be offset in time due to the volume of the sorbent cartridge and the time it takes fluid to flow from the inlet of the cartridge to the outlet. For example, a sorbent cartridge with a void volume of 4 liters will require 8 minutes for fluid to flow from the inlet to outlet at a flow rate of 500-mL/min. Therefore, the SCS value at 8 minutes should be compared to the PCS value at 0 minutes. The conductivity delta across the sorbent cartridge, SCS-PCS, is mainly influenced by the concentration of sodium bicarbonate entering the sorbent cartridge, which is determined by the prescription and patient parameters. In the low pH phase, all of the sodium bicarbonate entering the cartridge is removed resulting in a conductivity decrease. Because the SCS-PCS, or conductivity delta across the sorbent cartridge, can vary in the low pH phase due to difference in prescription or patient parameters, a plateau value can be calculated and subsequent conductivity deltas across the sorbent cartridge can be compared to the plateau value to determine when the pH has increased to the preset value. The plateau value can be determined by averaging the SCS-PCS values over a certain time, or dialysate volume, and starting at a particular dialysate volume. For example, after 40-liters of dialysate volume the SCS-PCS values, or the values calculated in Eq (1), can be averaged from to 50-liters. Then the conductivity delta across the sorbent cartridge (SCS-PCS) can be compared to the average plateau value to determine when the pH value has exceeded the preset value. For example, an increase in SCS-PCS of 0.44-mS/cm relative to the plateau value can indicate the pH has risen to a value exceeding 4.8. Values other than an increase of 0.44-mS/cm can be used depending on properties of the sorbent cartridge used or other factors such as dialysate prescription or patient parameters. The volume to start the averaging for the plateau value should start before the sorbent cartridge pH begins to rise. The volume can be based on the dialysate bicarbonate prescription. In a sorbent cartridge utilizing a zirconium phosphate sorbent as the pH controlling buffer source, the accumulation of bicarbonate through the sorbent cartridge will eventually exceed the buffering capacity of the zirconium phosphate and result in a rising pH. Therefore, a higher bicarbonate prescription will result in a sorbent cartridge pH rise sooner than a lower bicarbonate prescription. A bicarbonate prescription of 30-mM could start the plateau averaging at 60-liters and a bicarbonate prescription of 40-mM could start the plateau averaging at 40-liters, for example.

In certain embodiments, the sorbent cartridge effluent pH may remain below the preset pH value for the entire dialysis session. In such cases, the system can control the dialysate sodium and bicarbonate concentrations using the phase 1 method illustrated in FIG. 2 throughout the dialysis session. In certain embodiments, an acid source, such as a hydrochloric acid source, can be included upstream of the sorbent cartridge to acidify the dialysate prior to reaching the sorbent cartridge. Acidifying the dialysate can keep the sorbent cartridge effluent pH low, prolonging the time during which phase 1 control can be used. The low sorbent effluent pH can also be maintained by using a sufficient amount of zirconium phosphate at low pH, or by limiting the total volume of dialysate used during the dialysis session. In certain embodiments, the zirconium phosphate pH can refer to a slurry pH, which is the measured pH of zirconium phosphate slurried in water. A "low pH" zirconium phosphate can refer to zirconium phosphate having a slurry pH of below about 5.

Figure 3:
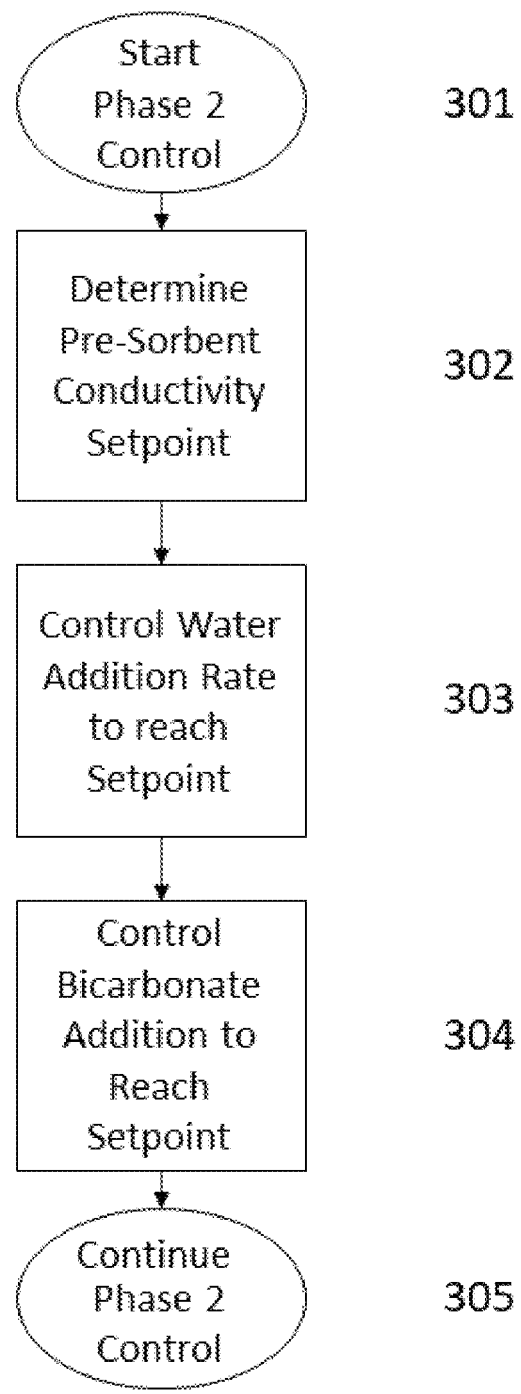
FIG. 3 is a flow chart showing a method of controlling sodium and bicarbonate during a high-pH phase.

As the pH rises above the preset pH, the amount of bicarbonate, post-degassing, can increase to greater than 1 mM, and potentially up to prescription levels of 30 to 40 mM, depending on the pH at sorbent outlet and the total $CO_2$ level in the spent dialysate entering the sorbent cartridge. During this second phase, the unpredictable bicarbonate level at sorbent outlet makes controlling to an accurate sodium and bicarbonate prescription level more difficult. FIG. 3 is a flow chart illustrating the phase 2 method of sodium and bicarbonate control in the dialysate with a higher pH in the dialysate exiting the sorbent cartridge. As described, the method can begin in step 301 using phase 2 control, after the sorbent cartridge effluent pH has exceeded the preset value.

In contrast to the phase 1 control illustrated in FIG. 2, the phase 2 control of FIG. 3 can use a pre-sorbent conductivity set point. In step 302, the system can determine the pre-sorbent conductivity set point as measured by conductivity sensor 111 illustrated in FIG. 1. The pre-sorbent conductivity set point is based on learning the sorbent inlet conductivity value used towards the end of the first phase of control. Over the course of a therapy session, the patient blood and the dialysate will approach equilibrium with each other, and the dialysate outlet conductivity measured by conductivity sensor 109 and subsequent sorbent inlet conductivity measured by conductivity sensor 111 will reach a stable value. Therefore, if the first phase of control occurs over a significant volume, i.e., greater than 30-liters, the pre-sorbent conductivity value can be assumed to have reached a stable value and can be used as the pre-sorbent conductivity set point for the second phase of control. In addition, the rate of change in the pre-sorbent conductivity (PCS), or PCS profile, can be learned during the first phase of control and used to control to a PCS profile in the second phase of control. For example, a steadily changing PCS value can be fit to a curve or a line and the PCS values to target as a function of dialysate volume can be extrapolated based on the fit during phase 2. Using the pre-sorbent conductivity set point determined in step 302, the system can control the water addition rate to achieve the pre-sorbent conductivity set point in step 303.

The phase 2 control can also rely on a predictable change in chloride concentration across the sorbent cartridge. In the case of the REDY type sorbent system, the chloride concentration can be assumed to be unchanged across the sorbent cartridge. Therefore, the PCS value determined in phase 1 is equal to the PCS value needed to achieve the desired chloride level, based on the dialysate prescription, at the sorbent inlet and subsequently the sorbent outlet, relying on the unchanging chloride concentration across the sorbent cartridge. The second aspect of control during the second phase involves adding sodium bicarbonate post-sorbent cartridge at a rate Q-Base to a conductivity value (BCS), which is the conductivity measured by conductivity sensor 116, based on the sodium and bicarbonate prescription value in step 304. Because the composition of dialysate needed after addition of sodium bicarbonate is accurately known based on the prescription, the composition error is minimized using this approach. Depending on the sorbent outlet pH and the total $CO_2$ exiting the sorbent cartridge, the bicarbonate concentration can vary be between 1 mM and 40 mM in concentration. Typically, in phase 2 the sorbent outlet pH will increase steadily resulting in a gradual increase of the bicarbonate concentration exiting the sorbent cartridge. Therefore, the amount of sodium bicarbonate that must be added to achieve the post-bicarbonate conductivity setpoint may vary. In step 305, the dialysis session can continue until the end of the session using the phase 2 control.

In certain embodiments, the system can use phase 1 control as long as possible before the sorbent cartridge effluent pH exceeds the preset value. Delaying the transition to phase 2 control as long as possible allows for further equilibration between the patient and dialysate and determination of a more accurate sorbent inlet conductivity setpoint or profile to be used during phase two control.

In some cases, there may be a need for an additional phase of control, between the first and second phases, due to release of sulfate from the sorbent cartridge. Some sorbent cartridge designs can remove sulfate when the sorbent cartridge is in a low pH phase, but as the pH rises (above 4.5 for example), the sulfate may be released. The release of sulfate will also result in the release of sodium, to maintain charge balance. At pH values above 3, sulfates primarily exist as a divalent anion and will require two sodium ions for charge balance. The release of sodium sulfate will result in a sorbent outlet conductivity increase that will require additional dilution water (Q-H2O) to maintain the sorbent outlet conductivity at the phase 1 set-point. However, because sulfate will be present in the sorbent outlet, an adjusted conductivity setpoint can be determined based on the methods used for phase one control, except with a non-zero level for sulfate, because although sulfate is being released due to slightly higher sorbent outlet pH, while the pH is still less than 4.8, the bicarbonate concentration is still negligible. Therefore, the sodium bicarbonate addition rate can be controlled using the phase 1 control illustrated in FIG. 2. However, the increased dilution water needed during sulfate release will result in a lower sorbent inlet conductivity (PCS) value, which is not indicative of the value needed for phase two control. Therefore, if sulfate release occurs, the pre-sorbent conductivity set-point used for phase two control should be based on the value, or profile, preceding the sulfate release. The sulfate release can be detected by monitoring changes in the dilution water rate and/or changes in the conductivity change across the sorbent cartridge. The sulfate release can be detected using the methods described above using the average plateau conductivity value and an increase relative to the average plateau value of 0.2-mS/cm. Values other than an increase of 0.2-mS/cm can be used depending on properties of the sorbent cartridge used or other factors such as dialysate prescription or patient parameters. The end of the sulfate release phase and the start of the second control phase can also be based on dilution water changes and/or sorbent cartridge conductivity changes, or can be based on a fixed volume, such as 5 or 10 liters of dialysate. In the case of using sorbent conductivity changes to determine the end of the sulfate release phase, the sorbent conductivity delta can continue to be monitored relative to the average plateau value and when it increases to a value of 0.44-mS/cm above the plateau value the sulfate release phase can be considered complete and the pH value above the phase 1 preset value. Any of the methods described for monitoring changes in sorbent cartridge effluent pH can also be used to determine if or when sulfate release occurs.

Figure 4:
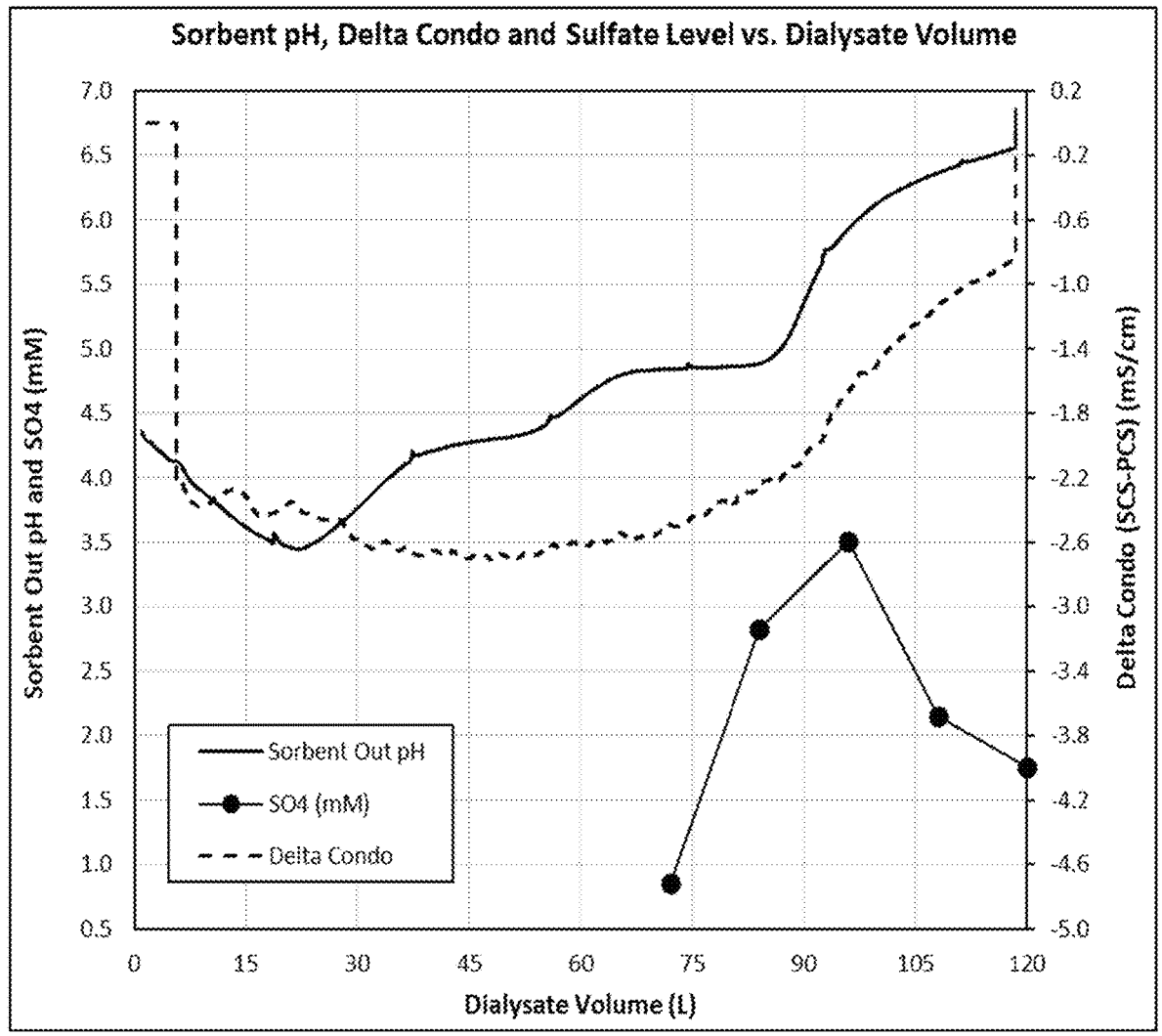
FIG. 4 is a graph showing sorbent pH, conductivity changes, and sulfate level vs. dialysate volume for a simulated dialysis session.
Figure 5:
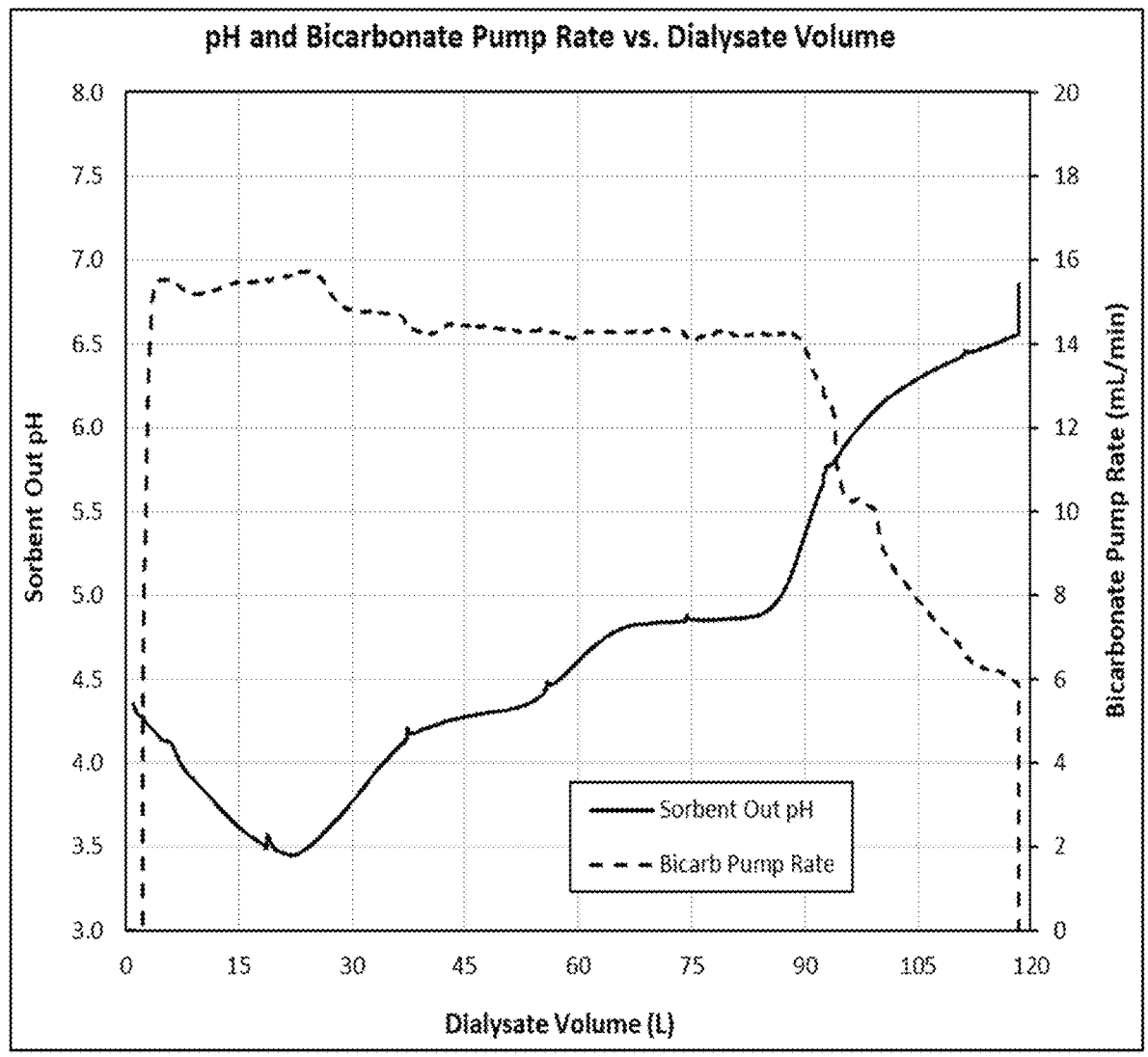
FIG. 5 is a graph showing sorbent outlet pH and bicarbonate pump rate vs. dialysate volume for a simulated dialysis session.
Figure 6:
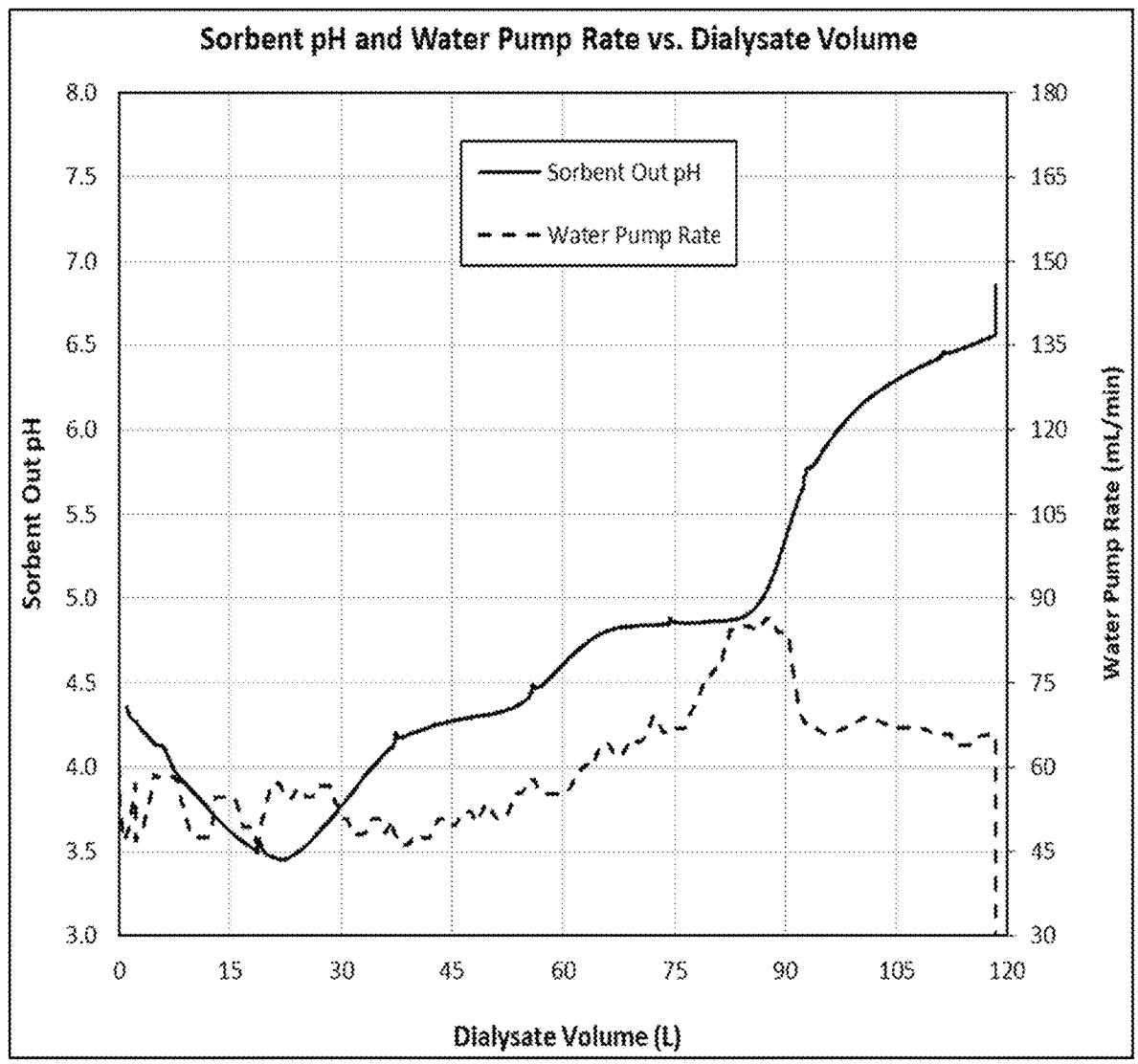
FIG. 6 is a graph showing sorbent outlet pH and water pump rate vs. dialysate volume for a simulated dialysis session.
Figure 7:
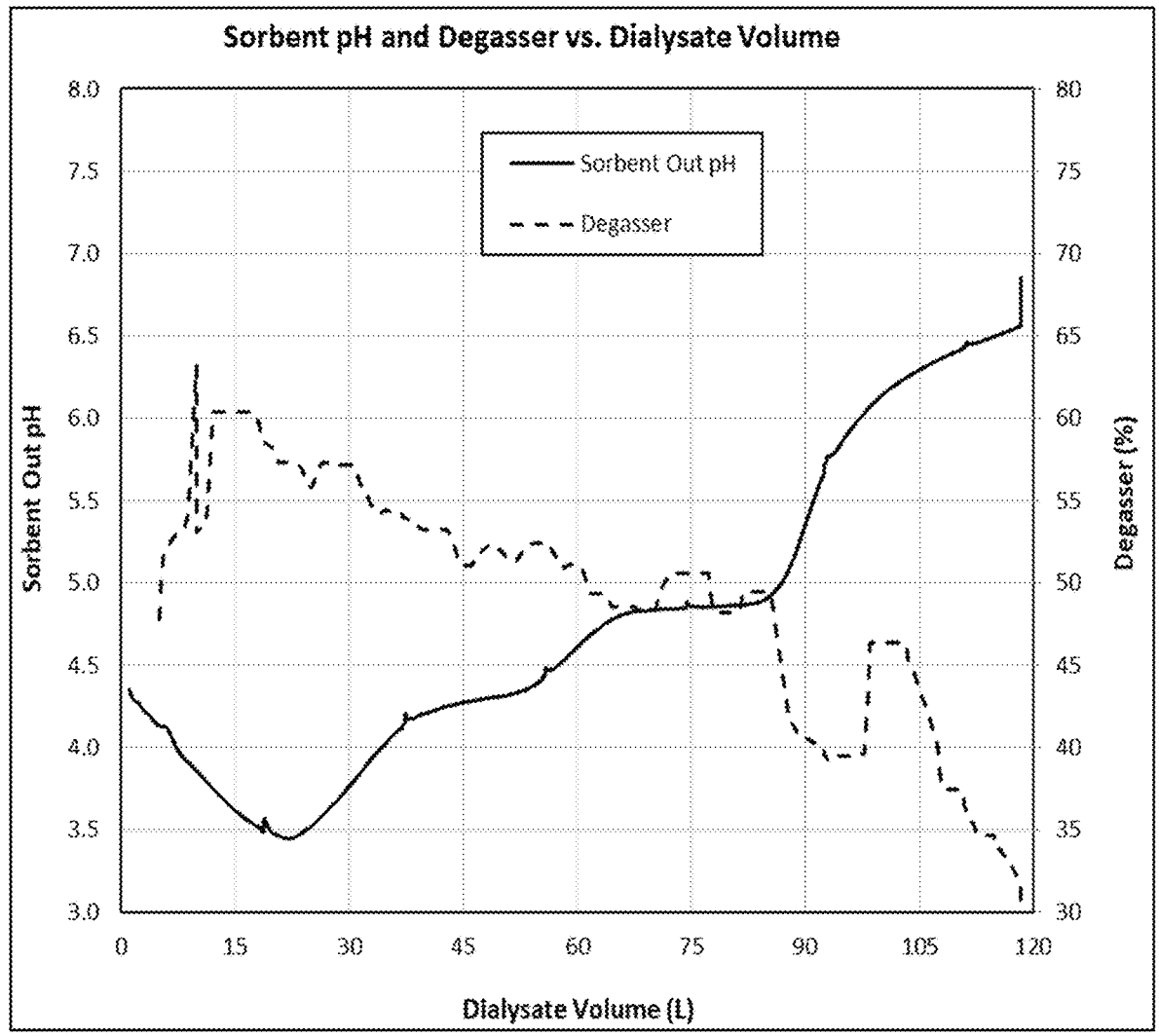
FIG. 7 is a graph showing sorbent outlet pH and degasser pump output vs. dialysate volume for a simulated dialysis session.
Figure 8:
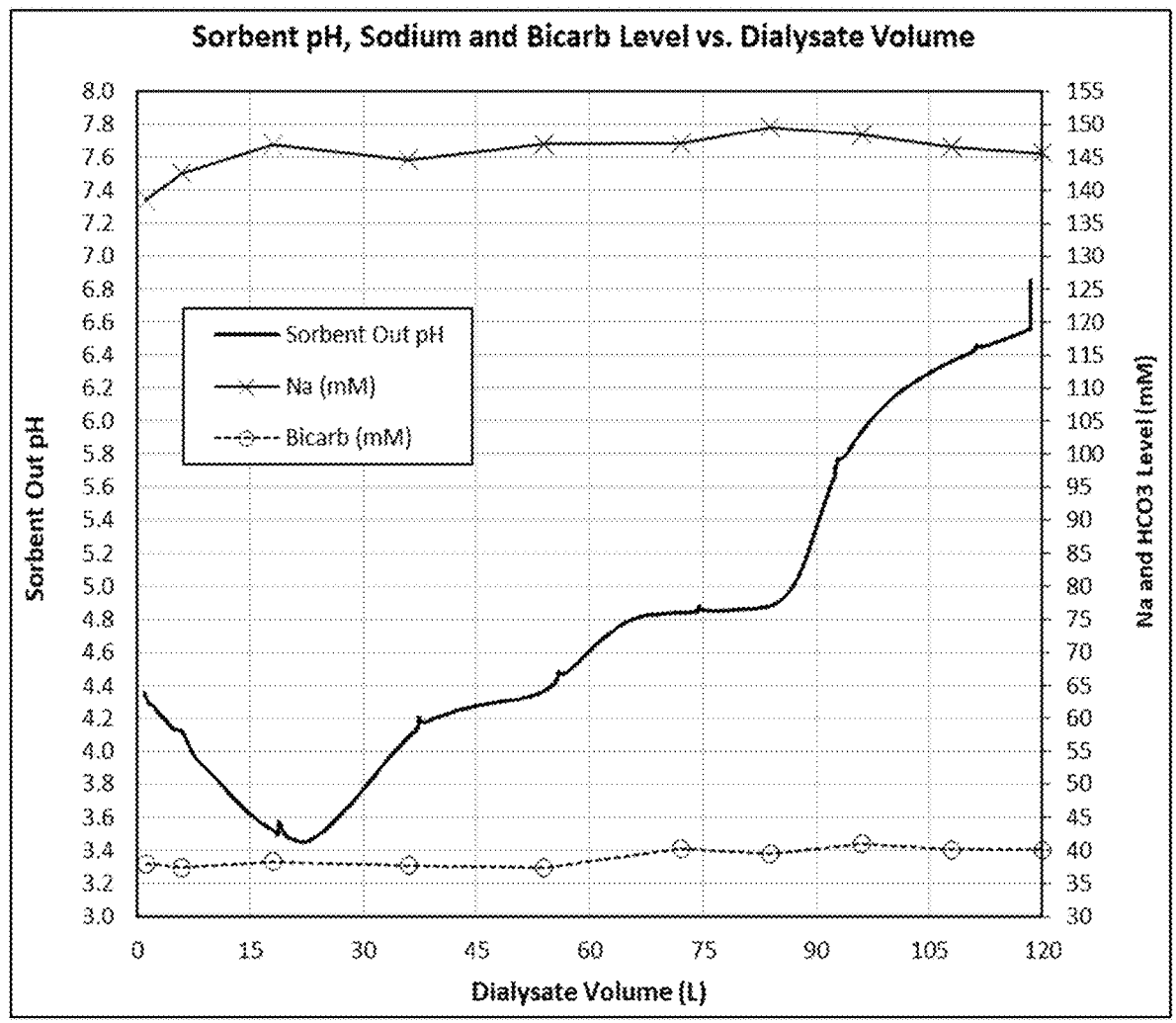
FIG. 8 is a graph showing sorbent outlet pH, dialysate sodium level, and dialysate bicarbonate level vs. dialysate volume for a simulated dialysis session

An example of the control approach utilized a prototype hemodialysis test system configured the same as FIG. 1, with the addition of a pH sensor between the sorbent cartridge and degasser. A simulated patient 18-liter patient tank was connected to the dialyzer (Clearum HS13) and recirculated through inlet 103 and outlet 104 at a rate of 500-mL/min. The dialysate was recirculated at a flow rate of 600-mL/min through the dialyzer at inlet 106 and outlet 107. The dialysate was controlled to a prescription composition target of 145-mM sodium, 40-mM bicarbonate, 2-mM potassium, 1.5-mM calcium and 0.375-mM magnesium. The patient had a composition of 131-mM sodium, 34.1-mM bicarbonate, 3.6-mM sulfate, 5-mM potassium, 0.4-mM magnesium, 1.3-mM calcium and 33-mM urea. The sorbent cartridge used contained activated carbon, urease, activated alumina, zirconium phosphate and hydrous zirconium oxide. A 200-minute simulated therapy was performed. FIG. 4 shows the sorbent outlet pH profile versus the cumulative dialysate volume during the simulated therapy. The pH stayed below 5 for the first 80-liters of dialysate and then increased to 6.5 by the end of therapy at 120-liters of dialysate. Also, shown in FIG. 4 is the delta conductivity across the sorbent cartridge calculated using equation 1. Finally, the sulfate level in the dialysate is shown over the course of therapy, where levels start to increase at 70-liters, peak at 97-liters and then start to decrease. For this simulated therapy, a plateau delta conductivity value of −2.59-mS/cm was calculated by averaging the delta conductivity from 60 to 65-liters. In order to determine when sulfate release occurred, and adjust the SCS conductivity target, a value of 0.2-mS/cm was used to compare to the plateau delta condo value. Using this value, the sulfate release was detected at 77-liters, which corresponds to a level of 1.5-mM sulfate as shown in FIG. 4. In order to determine when the pH exceeded a preset value of 4.9, and switch to phase 2 control, a value of 0.44 was used to compare to the plateau delta conductivity value. Using this value, a pH of 4.9 was predicted to occur at 88-liters, compared to the measured pH of 5.0 at 88-liters. The phase two control started at 88-liters and the bicarbonate metering rate (1000-mM solution of sodium bicarbonate shown as Q-Base in FIG. 1) over the course of therapy is shown in FIG. 5, along with the sorbent outlet pH profile. As shown in FIG. 5, the bicarbonate pump rate steadily decreases after the start of phase 2 control due to the increasing sorbent outlet pH and the increase of bicarbonate at sorbent outlet, requiring less bicarbonate to be metered in to meet the prescription of 40-mM bicarbonate. The bicarbonate metering rate is relatively constant during the low pH phase from 0 to 88-liters. FIG. 6 shows the water pump metering rate (Q-H$_2$O in FIG. 1) and sorbent outlet pH profile versus dialysate volume. As can be seen, as the pH starts to rise and the sulfate release starts to occur at 75-liters, the water metering starts to increase more rapidly. This increased water metering rate could also be used to predict when the sulfate release and preset pH value are reached. FIG. 7 shows the degasser pump output along with the sorbent outlet pH profile over the course of therapy. When the pH starts to rise above 4.9, the degasser output % decreases rapidly from about 50% to 40% when the pH increases from about 4.9 to 5.5. This change in degasser output could also be used to indicate when the preset pH value has been exceeded. FIG. 8 shows the measured dialysate sodium and bicarbonate levels along with the pH profile over the course of therapy. The target sodium level of 145-mM and the target bicarbonate (HCO3) level of 40-mM were achieved throughout therapy within 5% or better of target. Even during the rapid pH increase out of the sorbent cartridge starting at 85-liters, when the bicarbonate level leaving the sorbent cartridge starts to increase.

One of skill in the art will understand the data used in FIGS. 4-8 are from a simulated patient and provided for illustrative purposes only. The same methods can be used with any patient to accurately control the sodium and bicarbonate content of the dialysate.

One skilled in the art will understand that various combinations and/or modifications and variations can be made in the described systems and methods depending upon the specific needs for operation. Various aspects disclosed herein may be combined in different combinations than the combinations specifically presented in the description and accompanying drawings. Moreover, features illustrated or described as being part of an aspect of the disclosure may be used in the aspect of the disclosure, either alone or in combination, or follow a preferred arrangement of one or more of the described elements. Depending on the example, certain acts or events of any of the processes or methods described herein may be performed in a different sequence, may be added, merged, or left out altogether (e.g., certain described acts or events may not be necessary to carry out the techniques). In addition, while certain aspects of this disclosure are described as performed by a single module or unit for purposes of clarity, the techniques of this disclosure may be performed by a combination of units or modules associated with, for example, a medical device.

What is claimed is:
1. A system, comprising:
  a dialysate flow path; the dialysate flow path fluidly connectable to a dialysate inlet of a dialyzer and a dialysate outlet of the dialyzer;
  a sorbent cartridge in the dialysate flow path;

a degasser in the dialysate flow path downstream of the sorbent cartridge;

a bicarbonate source fluidly connected to the dialysate flow path;

a water source fluidly connected to the dialysate flow path;

a first conductivity sensor downstream of the sorbent cartridge; and a control system; the control system programmed to determine a pH of a fluid exiting the sorbent cartridge; wherein:

while pH of the fluid exiting the sorbent cartridge is below a preset pH, the control system is programmed to control a sodium concentration in the fluid based on a sodium prescription and a conductivity measured by the first conductivity sensor; and to control a bicarbonate concentration in the fluid based on a bicarbonate prescription; and while pH of the fluid exiting the sorbent cartridge is above a preset pH, the control system controls a sodium concentration in the fluid based on a sodium prescription and a conductivity measured by a second conductivity sensor upstream of the sorbent cartridge.

2. The system of claim 1, wherein the preset pH is about 4.8.

3. The system of claim 1, wherein the sorbent cartridge includes zirconium phosphate at a low pH.

4. The system of claim 1, wherein while the pH of the fluid exiting the sorbent cartridge is below the preset pH, the control system is programmed to control the sodium concentration in the fluid by adding water from a water source upstream of the sorbent cartridge to a target post-sorbent conductivity setpoint.

5. The system of claim 1, wherein while the pH of the fluid exiting the sorbent cartridge is below the preset pH, the control system is programmed to control the bicarbonate concentration in the fluid by adding bicarbonate from a bicarbonate source upstream of the sorbent cartridge to a target post-bicarbonate conductivity setpoint.

6. The system of claim 1, further comprising a hydrochloric acid source fluidly connected to the dialysate flow path upstream of the sorbent cartridge.

7. The system of claim 1, further comprising at least one infusate source downstream of the sorbent cartridge.

8. The system of claim 1, wherein the control system is programmed to detect release of sulfate ions from the sorbent cartridge.

9. The system of claim 8, wherein the control system is programmed to dilute the fluid during the release of sulfate ions.

10. The system of claim 1, wherein while the pH of the fluid exiting the sorbent cartridge is above the preset pH, the control system is programmed to control the sodium concentration in the fluid by adding water from a water source upstream of the sorbent cartridge to a target pre-sorbent conductivity setpoint.

11. The system of claim 10, wherein the target pre-sorbent conductivity setpoint is a conductivity measured upstream of the sorbent cartridge while the pH is below the preset pH.

12. The system of claim 10, wherein while the pH of the fluid exiting the sorbent cartridge is above the preset pH, the control system is programmed to control the bicarbonate concentration in the fluid by adding bicarbonate to reach a target post-bicarbonate conductivity setpoint.

13. The system of claim 12, wherein the target post-bicarbonate conductivity setpoint is based on the sodium and a bicarbonate prescription.

14. The system of claim 1, wherein the pH of the fluid exiting the sorbent cartridge is measured with a pH sensor downstream of the sorbent cartridge.

15. The system of claim 1, wherein the pH of the fluid exiting the sorbent cartridge is measured based on changes to a degasser output.

16. The system of claim 1, wherein the pH of the fluid exiting the sorbent cartridge is measured based on a conductivity change across the sorbent cartridge measured by the first conductivity sensor and a second conductivity sensor upstream of the sorbent cartridge.

17. The system of claim 4, wherein the pH of the fluid exiting the sorbent cartridge is measured based on a volume of the water added from the water source.

18. The system of claim 1, the control system programmed to isolate the sorbent cartridge prior to determining the pH of the fluid exiting the sorbent cartridge.

* * * * *